(12) United States Patent
Hunt

(10) Patent No.: US 10,898,478 B2
(45) Date of Patent: *Jan. 26, 2021

(54) GLUCOCORTICOID RECEPTOR MODULATORS TO TREAT CERVICAL CANCER

(71) Applicant: Corcept Therapeutics, Inc., Menlo Park, CA (US)

(72) Inventor: Hazel Hunt, Storrington (GB)

(73) Assignee: Corcept Therapeutics, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/742,198

(22) Filed: Jan. 14, 2020

(65) Prior Publication Data

US 2020/0147073 A1 May 14, 2020

Related U.S. Application Data

(63) Continuation of application No. 16/185,271, filed on Nov. 9, 2018, now Pat. No. 10,568,880, which is a continuation of application No. 15/942,312, filed on Mar. 30, 2018, now Pat. No. 10,413,540.

(60) Provisional application No. 62/480,226, filed on Mar. 31, 2017.

(51) Int. Cl.
   *A61K 31/4745* (2006.01)
   *A61K 31/337* (2006.01)
   *A61P 35/00* (2006.01)

(52) U.S. Cl.
   CPC ........ *A61K 31/4745* (2013.01); *A61K 31/337* (2013.01); *A61P 35/00* (2018.01)

(58) Field of Classification Search
   CPC .................................................. A61K 31/4745
   See application file for complete search history.

(56) References Cited

U.S. PATENT DOCUMENTS

| | | | |
|---|---|---|---|
| 4,963,558 A | 10/1990 | Hotten et al. | |
| 5,696,127 A | 12/1997 | Jones et al. | |
| 6,583,180 B2 | 6/2003 | Link et al. | |
| 6,680,310 B2 | 1/2004 | Belanoff et al. | |
| 7,576,076 B2 | 8/2009 | Clark et al. | |
| 7,678,813 B2 | 3/2010 | Clark et al. | |
| 7,790,745 B2 | 9/2010 | Yang et al. | |
| 7,799,782 B2 | 9/2010 | Munson et al. | |
| 7,928,237 B2 | 4/2011 | Clark et al. | |
| 8,003,689 B2 | 8/2011 | Veverka | |
| 8,173,674 B2 | 5/2012 | Keil et al. | |
| 8,461,172 B2 | 6/2013 | Clark et al. | |
| 8,598,154 B2 | 12/2013 | Clark et al. | |
| 8,658,128 B2 | 2/2014 | Altschul et al. | |
| 8,685,973 B2 | 4/2014 | Clark et al. | |
| 8,710,035 B2 | 4/2014 | Pan et al. | |
| 8,859,774 B2 | 10/2014 | Hunt et al. | |
| 8,969,557 B2 | 3/2015 | Harriman et al. | |
| 9,114,147 B2 | 8/2015 | Altschul et al. | |
| 9,149,485 B2 | 10/2015 | Pan et al. | |
| 9,273,047 B2 | 3/2016 | Walters et al. | |
| 9,289,436 B2 | 3/2016 | Szmulewitz et al. | |
| 9,314,473 B2 | 4/2016 | Altschul et al. | |
| 9,320,747 B1 | 4/2016 | Altschul et al. | |
| 9,422,323 B2 | 8/2016 | Houpis et al. | |
| 9,623,032 B2 | 4/2017 | Pan et al. | |
| 9,707,223 B2 | 7/2017 | Hunt et al. | |
| 9,801,893 B2 | 10/2017 | Szmulewitz et al. | |
| 9,829,495 B2 | 11/2017 | Moraitis | |
| 9,943,505 B2 * | 4/2018 | Hunt | A61K 31/44 |
| 9,956,216 B2 | 5/2018 | Hunt et al. | |
| 10,047,082 B2 | 8/2018 | Hunt et al. | |
| 10,117,852 B2 * | 11/2018 | Hunt | A61K 31/416 |
| 10,213,414 B2 * | 2/2019 | Hunt | A61K 45/06 |
| 10,413,540 B2 * | 9/2019 | Hunt | A61P 35/00 |
| 10,456,392 B2 | 10/2019 | Hunt et al. | |
| 10,568,880 B2 * | 2/2020 | Hunt | A61P 35/00 |
| 2002/0115613 A1 | 8/2002 | Kumar | |
| 2004/0102422 A1 | 5/2004 | Gaston | |
| 2005/0124533 A1 | 6/2005 | Schatzberg et al. | |
| 2006/0063748 A1 | 3/2006 | Belanoff | |
| 2007/0128627 A1 | 6/2007 | Simons, Jr. et al. | |
| 2007/0281928 A1 | 12/2007 | Clark et al. | |

(Continued)

FOREIGN PATENT DOCUMENTS

| | | |
|---|---|---|
| EP | 145121 A2 | 6/1985 |
| EP | 375210 A1 | 6/1990 |

(Continued)

OTHER PUBLICATIONS

Benagiano et al., "Selective Progesterone Receptor Modulators 3: Use in Oncology, Endocrinology and Psychiatry", Expert Opin. Pharmacother, vol. 9, Issue 14, Oct. 2008, pp. 2487-2496.

Block et al., "Glucocorticoid Receptor Expression in 20 Solid Tumor Types Using Immunohistochemistry Assay", Cancer Management and Research, vol. 9, Mar. 6, 2017, pp. 65-72.

Check et al., "Evidence that Mifepristone, A Progesterone Receptor Antagonist, Can Cross the Blood Brain Barrier and Provide Palliative Benefits for Glioblastoma Multiforme Grade IV", Anticancer Research, vol. 34, No. 5, May 2014, pp. 2385-2388.

Check et al., "Mifepristone Causing Complete Remission of Rapidly Advancing Leukemia with Measurement of Progesterone-induced Blocking Factor", Anticancer Research, vol. 34, No. 5, May 2014, pp. 2413-2416.

Chen et al., "Mechanism of the Reversal Effect of Mifepristone on Drug Resistance of the Human Cervical Cancer Cell Line HELA/MMC", Genetics and Molecular Research, vol. 13, No. 1, 2014, pp. 1288-1295.

(Continued)

*Primary Examiner* — Rei Tsang Shiao
(74) *Attorney, Agent, or Firm* — Kilpatrick Townsend & Stockton LLP

(57) ABSTRACT

Methods for treating a subject having a cancerous tumor are disclosed. The methods comprise administering to the subject an effective amount of a non-steroidal selective glucocorticoid receptor modulator (SGRM) and an effective amount of a chemotherapeutic agent. The tumor may be cervical cancer. The SGRM may be a fused azadecalin. In embodiments, the SGRM may be a heteroaryl ketone fused azadecalin or an octahydro fused azadecalin.

20 Claims, 3 Drawing Sheets

(56) References Cited

U.S. PATENT DOCUMENTS

| | | |
|---|---|---|
| 2008/0070950 A1 | 3/2008 | Benjamin et al. |
| 2008/0287419 A1 | 11/2008 | Bruncko et al. |
| 2009/0156672 A1 | 6/2009 | Budunova et al. |
| 2010/0135956 A1 | 6/2010 | Gant et al. |
| 2010/0179115 A1 | 7/2010 | Belanoff |
| 2010/0292477 A1 | 11/2010 | Clark et al. |
| 2011/0166110 A1 | 7/2011 | Clark et al. |
| 2011/0269728 A1 | 11/2011 | Pan et al. |
| 2012/0022121 A1 | 1/2012 | Dalton et al. |
| 2012/0201747 A1 | 8/2012 | Altschul et al. |
| 2012/0220565 A1 | 8/2012 | Clark et al. |
| 2013/0225633 A1 | 8/2013 | Hunt et al. |
| 2014/0038926 A1 | 2/2014 | Hunt et al. |
| 2015/0080389 A1 | 3/2015 | Hunt et al. |
| 2016/0215049 A1 | 7/2016 | Feldhaus et al. |
| 2017/0020860 A1 | 1/2017 | Hunt et al. |
| 2017/0273972 A1 | 9/2017 | Hunt et al. |
| 2018/0193313 A1 | 7/2018 | Hunt et al. |
| 2018/0280378 A1 | 10/2018 | Hunt |
| 2019/0076424 A1 | 3/2019 | Hunt |

FOREIGN PATENT DOCUMENTS

| | | |
|---|---|---|
| JP | 09505030 A | 5/1997 |
| JP | 2002506032 A | 2/2002 |
| JP | 2002544271 A | 12/2002 |
| WO | 9504734 A1 | 2/1995 |
| WO | 9945925 A1 | 9/1999 |
| WO | 0069846 A1 | 11/2000 |
| WO | 03015692 A2 | 2/2003 |
| WO | 03061651 A1 | 7/2003 |
| WO | 2005087769 A1 | 9/2005 |
| WO | 2009064738 A2 | 5/2009 |
| WO | 2012027702 A1 | 3/2012 |
| WO | 2013039916 A1 | 3/2013 |
| WO | 2013177559 A2 | 11/2013 |
| WO | 2013177559 A3 | 1/2014 |
| WO | 2015077530 A1 | 5/2015 |
| WO | 2016055533 A1 | 4/2016 |
| WO | 2016141365 A1 | 9/2016 |
| WO | 2017023694 A1 | 2/2017 |
| WO | 2017151613 A1 | 9/2017 |

OTHER PUBLICATIONS

Cossu et al., "The Role of Mifeprisione in Meningiomas Management: A Systematic Review of the Literature", BioMed Research International, vol. 2015, Article ID 267831, Jul. 2015, pp. 1-11.

Kach et al., "Glucocorticoid Receptor Signaling in Breast and Prostate Cancers: Emergence as a Therapeutic Target", Science Translational Medicine, vol. 7, No. 305, Sep. 16, 2015, pp. 1-9.

Kach et al., "Selective Glucocorticoid Receptor Modulators (SGRMs) Delay Castrate-Resistant Prostate Cancer Growth", Molecular Cancer Therapeutics, vol. 16, No. 8, Aug. 2017, pp. 1680-1692.

Kondo et al., "A Case of Ectopic Adrenocorticotropic Hormone-Producing Pancreatic Neuroendocrine Tumor with Multiple Liver Metastases", Endocr J., vol. 57, No. 3, Apr. 2010, pp. 229-236.

Norman et al., "Functional Glucocorticoid Receptor Modulates Pancreatic Carcinoma Growth through an Autocrine Loop", J. Surg. Res., vol. 57, No. 1, Jul. 1994, pp. 33-38.

Novotny et al., "Cancer Therapy: New Targets for Chemotherapy", Hematology, vol. 8, No. 3, Jun. 2003, pp. 129-137.

Schlossmacher et al., "Glucocorticoid Receptor-Mediated Apoptosis: Mechanisms of Resistance in Cancer Cells", Journal of Endocrinology, vol. 211, No. 1, Oct. 2011, pp. 17-25.

Segovia-Mendoza et al., "Antihormonal Agents as a Strategy to Improve the Effect of Chemo-Radiation in Cervical Cancer: In Vitro and in Vivo Study", BMC Cancer, vol. 15, No. 21, 2015, pp. 1-11.

Stringer-Reasor et al., "Glucocorticoid Receptor Activation Inhibits Chemotherapy-Induced Cell Death in High-Grade Serous Ovarian Carcinoma", Gynecol. Oncol., vol. 138, No. 3, Sep. 2015, pp. 656-662.

Touat et al., "Successful Treatment of Multiple Intracranial Meningiomas with the Antiprogesterone Receptor Agent Mifepristone (RU486)", Acta Neurochirurgica, vol. 156, No. 10, Oct. 2014, pp. 1831-1835.

West et al., "Abstract PD3-02: Second-Generation Selective Glucocorticoid Receptor Modulators in Triple-Negative Breast Cancer", Cancer Research, vol. 76, No. 4, Feb. 2016, 2 pages.

Yu et al., "Systems Pharmacology of Mifepristone (RU486) Reveals its 47 Hub Targets and Network: Comprehensive Analysis and Pharmacological Focus on FAK-Src-Paxillin complex", Scientific Reports, vol. 5, No. 7830, 2015, pp. 1-10.

Zhang et al., "Corticosteroid Co-Treatment Induces Resistance to Chemotherapy in Surgical Resections, Xenografts and Established Cell Lines of Pancreatic Cancer", BMC Cancer, vol. 6, No. 61, Mar. 15, 2006, pp. 1-14.

PCT/US2018/025547, "International Search Report and Written Opinion", dated Aug. 9, 2018, 13 pages.

Aherne, "Finding the Needle in the Haystack: Why Highthroughput Screening is Good for Your Health", Breast Cancer Research, vol. 4, No. 4, 2002, pp. 148-154.

Belova et al., "Glucocorticoid Receptor Expression in Breast Cancer Associates with Older Patient Age", Breast Cancer Res Treat, vol. 116, Issue 3, Aug. 2009, pp. 441-447.

Chen et al., "Androgen and Glucocorticoid Receptor Heterodimer Formation", J. Biol. Chem., vol. 272, No. 22, May 30, 1997, pp. 14087-14092.

Cho et al., "Role of Activation function Domain-1, DNA Binding, and Coactivator GRIP1 in the Expression of Partial Agonist Activity of Glucocorticoid Receptor-Antagonist Complexes", Biochemistry, vol. 44, Issue 9, 2005, pp. 3547-3561.

Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, Issue 4, Feb. 15, 2008, pp. 1312-1317.

Clark, "Glucocorticoid Receptor Antagonists", Current Topics in Medicinal Chemistry, vol. 8, Issue 9, Jun. 1, 2008, pp. 813-838.

Colleoni et al., "Response to Primary Chemotherapy in Breast Cancer Patients with Tumors Not Expressing Estrogen and Progesterone Receptors", Annals of Oncology, vol. 11, Issue 8, Aug. 1, 2000, pp. 1057-1059.

Damia et al., "Contemporary Pre-clinical Development of Anticancer Agents—What Are the Optimal Preclinical Models", European Journal of Cancer, vol. 45, No. 16, Nov. 2009, pp. 2768-2781.

Donovan et al., "Androgen Receptor Expression is Associated with Prostate Cancer-Specific Survival in Castrate Patients with Metastatic Disease", BJU International, vol. 105, Issue 4, Feb. 2010, pp. 462-467.

EP13793417.0, "Extended European Search Report", dated Jan. 4, 2016, 7 pages.

EP18154256.4, "Extended European Search Report", dated Mar. 26, 2018, 6 pages.

EP19188885.8, "Extended European Search Report", dated Oct. 28, 2019, 6 pages.

Gaddy et al., "Mifepristone Induces Growth Arrest, Caspase Activation, and Apoptosis of Estrogen Receptor-Expressing, Antiestrogen-Resistant Breast Cancer Cells", Clinical Cancer Research, vol. 10, Issue 15, Aug. 1, 2004, pp. 5215-5225.

Genck, Chemical Processing .com, 2004.

Grover et al., "The Initiation of Breast and Prostate Cancer", Carcinogenesis, vol. 23, Issue 7, Jul. 1, 2002, pp. 1095-1102.

Gulliver, "Xenobiotics and the Glucocorticoid Receptor", Toxicology and Applied Pharmacology, vol. 319, Mar. 15, 2017, pp. 69-79.

He et al., "Discovery of a Highly Potent Glucocorticoid for Asthma Treatment", Cell Discovery, vol. 1, No. 15035, 2015, 13 pages.

Hein et al., "Click Chemistry, A powerful Tool for Pharmaceutical Sciences", Pharmaceutical Research, vol. 25, Issue 10, Oct. 2008, pp. 2216-2230.

Henderson et al., "Estrogens as a Cause of Human Cancer: the Richard and Hinda Rosenthal Foundation Award Lecture", Cancer Research, vol. 48, Issue 2, Jan. 15, 1988, pp. 246-253.

Huang et al., "Reversal Effect of Mifepristone on Adriamycin Resistance in Human Breast Cancer Cell Line MCF-7/ADM in Vitro and in Vivo", J Cent South Univ (Med Sci), vol. 35, Issue 6, Jun. 2010, pp. 576-583.

(56) References Cited

OTHER PUBLICATIONS

Hunt et al., "Preclinical Efficacy of the Selective GR antagonist, CORT125134", American Association for Cancer Research, 2017, 1 page.
Jemal et al., "Cancer Statistics", CA: A Cancer Journal for Clinicians, vol. 60, Issue 5, Sep.-Oct. 2010, pp. 277-300.
Johnson et al., "Relationships Between Drug Activity in NCI Preclinical in Vitro and in Vivo Models and Early Clinical Trial", British Journal of Cancer, vol. 84, No. 10, May 18, 2001, pp. 1424-1431.
JP2007-503030 , "Office Action", dated Feb. 23, 2011, 8 pages.
Kadmiel et al., "Glucocorticoid Receptor Signaling in Health and Disease", Trends in Pharmacological Sciences, vol. 34, No. 9, Sep. 2013, pp. 518-530.
Keen et al., "The Biology of Breast Carcinoma", Cancer, vol. 97, No. 3, Feb. 1, 2003, pp. 825-833.
Klein et al., "Analyzing Survival Curves at a Fixed Point in Time", Stat. Med., vol. 26, Issue 24, Oct. 30, 2007, pp. 4505-4519.
Klijn et al., "Antiprogestins a New Form of Endocrine Therapy for Human Breast Cancer", Cancer Research, vol. 49, Issue 11, Jun. 1, 1989, pp. 2851-2856.
Kriaucionis et al., "The Nuclear DNA Base 5-Hydroxymethylcytosine is Present in Brain and Enriched in Purkinje Neurons", Science, vol. 324, No. 5929, May 15, 2009, 5 pages.
Loi et al., "Definition of Clinically Distinct Molecular Subtypes in Estrogen Receptor-Positive Breast Carcinomas Through Genomic Grade", Journal of Clinical Oncology, vol. 25, No. 10, Apr. 1, 2007, pp. 1239-1246.
Loi et al., "Predicting Prognosis Using Molecular Profiling in Estrogen Receptor-Positive Breast Cancer Treated With Tamoxifen", BMC Genomics, vol. 9, No. 239, May 22, 2008, pp. 1-12.
Lucci et al., "Modification of Ceramide Metabolism Increases Cancer Cell Sensitivity to Cytotoxics", Int J. Onco., vol. 15 Issue 3, Sep. 1999, pp. 541-546.
Ma et al., "IL-21 Activates Both Innate and Adaptive Immunity to Generate Potent Antitumor Responses that Require Perforin but Are Independent of IFN-Gamma", J. Jmmunol, vol. 171, Issue 2, Jul. 15, 2003, pp. 608-615.
Melhem et al., "Administration of Glucocorticoids to Ovarian Cancer Patients is Associated with Expression of the Anti-apoptotic Genes SGK1 and MKP1/DUSP1 in Ovarian Tissues", Clinical Cancer Research, vol. 15, No. 9, May 1, 2009, pp. 3196-3204.
Mikosz et al., "Glucocorticoid Receptor-Mediated Protection from Apoptosis is Associated with Induction of the Serine/Threonine Survival Kinase Gene, sgk-1", The Journal of Biological Chemistry, vol. 276, No. 20, Feb. 13, 2001, pp. 16649-16654.
Minn et al., "Genes that Mediate Breast Cancer Metastasis to Lung", Nature. vol. 436, No. 7050, Jul. 28, 2005, pp. 518-524.
Moller et al., "Impact of New Technologies for Cellular Screening along the Drug Value Chain", Drug Discovery Today, vol. 14, No. 9/10, May 2010, pp. 384-390.
Moran et al., "The Glucocorticoid Receptor Mediates a Survival Signal in Human Mammary Epithelial Cells", Cancer Research, vol. 60, Issue 4, Feb. 15, 2000, pp. 867-872.
Moses et al., "The Growing Applications of Click Chemistry", Chem Soc Rev., vol. 36, Issue 8, May 2007, pp. 1249-1262.
Munster et al., "A Phase 1/2 Study of Relacorilant + Nab-Paclitaxel (Nabpac) in Patients (Pts) with Solid Tumors: The Dose-Finding Phase", Journal of Clinical Oncology, vol. 36, No. 15, May 20, 2018, 4 pages.
Munster et al., "A Phase 1/2 Study of Relacorilant + Paclitaxel in Patients with Solid Tumors: The Dose-Finding Phase", American Association for Cancer Research, 2018, 1 page.
MYPI2014003289 , "Substantive Examination Adverse Report", dated Mar. 30, 2018, 2 pages.
Niemeier et al., "Androgen Receptor in Breast Cancer: Expression in Estrogen Receptor-Positive Tumors and in Estrogen Receptor-Negative Tumors with Apocrine Differentiation", Mod Pathol., vol. 23, No. 2, 2010, pp. 205-212.

Ocana et al., "Preclined Development of Molecular-targeted Agents for Cancer", Nature Reviews Clinical Oncologyreview, vol. 8, No. 4, Apr. 2011, pp. 200-209.
Pan et al., "Activation of the Glucocorticoid Receptor is Associated with Poor Prognosis in Estrogen Receptor-Negative Breast Cancer", Cancer Research, vol. 71, No. 20, Oct. 15, 2011, 21 pages.
Pang et al., "Dexamethasone Decreases Xenograft Response to Paclitaxel Through Inhibition of Tumor Cell Apoptosis", Cancer Biology & Therapy, vol. 5, Issue 8, Aug. 2006, pp. 933-940.
PCT/US13/27720 , "International Search Report and Written Opinion", dated Jun. 17, 2013, 9 pages.
PCT/US2005/0008049 , "International Search Report", dated Jun. 15, 2005.
PCT/US2010/034382 , "International Search Report and Written Opinion", dated Jul. 9, 2010, 7 pages.
PCT/US2011/49408 , "International Search Report and Written Opinion", dated Jan. 30, 2012, 10 pages.
PCT/US2013/027150 , "International Preliminary Report on Patentability", dated Sep. 4, 2014, 7 pages.
PCT/US2013/027150 , "International Search Report and Written Opinion", dated Apr. 29, 2013, 9 pages.
Peeters et al., "Differential Effects of the New Glucocorticoid Receptor Antagonist ORG 34517 and RU486 (Mifepristone) on Glucocorticoid Receptor Nuclear Translocation in the AtT20 Cell Line", Ann. NY Acad. Sci., vol. 1148, Issue 1, Dec. 2008, pp. 536-541.
Pike et al., "Estrogens, Progestogens, Normal Breast Cell Proliferation, and Breast Cancer Risk", Epidemiologic Rev., vol. 15, Issue 1, Jan. 1, 1993, pp. 17-30.
Ring et al., "Mechanisms of Tamoxifen Resistance", Endocrine-Related Cancer, vol. 11, Issue 4, Dec. 2004, pp. 643-658.
Robinson et al., "Octahydrophenanthrene-2,7-diol Analogues as Dissociated Glucocorticoid Receptor Agonists: Discovery and Lead Exploration", J. Med. Chem., vol. 52, No. 6, 2009, pp. 1731-1743.
Sahoo et al., "Coordinate Expression of the PI3-Kinase Downstream Effectors Serum and Glucocorticoid-Induced Kinase (SGK-1) and Akt-1 in Human Breast Cancer", European Journal of Cancer, vol. 41, Issue 17, Nov. 2005, pp. 2754-2759.
Schenone et al., "Target Identification and Mechanism of Action in Chemical Biology and Drug Discovery", Nature Chemical Biology, vol. 9, No. 4, 2013, pp. 232-240.
Sharma et al., "Cell Line-based Platforms to Evaluate the Therapeutic Efficacy of Candidate Anticancer Agents", Nature Reviews Cancer, vol. 10, No. 4, Apr. 2010, pp. 241-253.
Sims et al., "The Removal of Multiplicative, Systematic Bias Allows Integration of Breast Cancer Gene Expression Datasets—Improving Meta-Analysis and Prediction of Prognosis", BMC Medical Genomics, vol. 1, No. 42, Sep. 21, 2008, pp. 1-14.
Smith et al., "Expression of Glucocorticoid and Progesterone Nuclear Receptor Genes in Archival Breast Cancer Tissue", Breast Cancer Research, vol. 5, Issue 1, 2003, pp. R9-R12.
Smith et al., "Progesterone, Glucocorticoid, but not Estrogen Receptor mRNA is Altered in Breast Cancer Stroma", Cancer Letters, vol. 255, Issue 1, Sep. 18, 2007, pp. 77-84.
Sorlie et al., "Gene Expression Patterns of Breast Carcinomas Distinguish Tumor Subclasses with Clinical Implications", Proc. Nat. Acad. Sci., vol. 98, No. 19, Sep. 11, 2001, pp. 10869-10874.
Sotiriou et al., "Gene Expression Profiling in Breast Cancer: Understanding the Molecular Basis of Histologic Grade to Improve Prognosis", Journal of the National Cancer Institute, vol. 98, No. 4, Feb. 15, 2006, pp. 262-272.
Srinivas et al., "Proteomics for Cancer Biomarker Discovery", Clinical Chemistry, vol. 48, Issue 8, Aug. 2002, pp. 1160-1169.
Sui et al., "Estrogen Receptor α Mediates Breast Cancer Cell Resistance to Paclitaxel through Inhibition of Apoptotic Cell Death", Cancer Research, vol. 67, Issue 11, Jun. 1, 2007, pp. 5337-5344.
Sundahl et al., "Selective Glucocorticoid Receptor-Activating Adjuvant Therapy in Cancer Treatments", Oncoscience, vol. 3, No. 7-8, Jul. 2016, pp. 188-202.
Tessier et al., "Serum and Glucocorticoid-Regulated Protein Kinases: Variations on a Theme", Journal of Cellular Biochemistry, vol. 98, Issue 6, Aug. 15, 2006, pp. 1391-1407.

(56) References Cited

OTHER PUBLICATIONS

Venkatesh et al., "Role of the Development Scientist in Compound Lead Selection and Optimization", Journal of Pharmaceutical Sciences, vol. 89, Issue 2, Feb. 2000, pp. 145-154.
Wang et al., "Gene-Expression Profiles to Predict Distant Metastasis of Lymph-Node-Negative Primary Breast Cancer", The Lancet, vol. 365, Issue 9460, Feb. 19-25, 2005, pp. 671-679.
Wu et al., "Glucocorticoid Receptor Activation Signals through Forkhead Transcription Factor 3a in Breast Cancer Cells", Mol. Endocrinol, vol. 20, No. 10, Oct. 1, 2006, pp. 2304-2314.
Wu et al., "Microarray Analysis Reveals Glucocorticoid-Regulated Survival Genes that are Associated with Inhibition of Apoptosis in Breast Epithelial Cells", Cancer Research, vol. 64, Issue 5, Mar. 1, 2004, pp. 1757-1764.
Application No. EP18777520.0, Extended European Search Report, dated Jul. 16, 2020, 9 pages.
"Study of Relacorilant in Combination with Nab-Paclitaxel for Patients with Recurrent Platinum-Resistant Ovarian, Fallopian Tube, or Primary Peritoneal Can", ClinicaiTrials.gov, Available online at: www.clinicaltrials.gov/ct2/show/NCT03776812, Retrieved: Apr. 30, 2019, 11 pages.
"Study to Evaluate Corti 25134 in Combination with Nab-Paclitaxel in Patients with Solid Tumors", ClinicaiTrials.gov, Available online at: www.clinicaltrials.gov/ct2/show/NCT02762981, Retrieved: Apr. 30, 2019, 7 pages.

\* cited by examiner

GLUCOCORTICOID RECEPTOR MODULATORS TO TREAT CERVICAL CANCER

CROSS-REFERENCE TO RELATED APPLICATION

This application claims priority to, and the benefit of, U.S. patent application Ser. No. 16/185,271, filed Nov. 9, 2018, which is a continuation of U.S. patent application Ser. No. 15/942,312, filed Mar. 30, 2018, now U.S. Pat. No. 10,413,540, which claims priority to, and the benefit of, U.S. Provisional Patent Application Ser. No. 62/480,226, filed Mar. 31, 2017, which applications are hereby incorporated by reference herein in their entireties.

BACKGROUND

Cancer is a leading cause of death in the United States. For example, cervical cancer often has a poor prognosis, even when diagnosed early, and signs and symptoms may not appear until the cancer is quite advanced and complete surgical removal is not possible.

Conventional treatment options for cancers such as cervical cancer include surgery, radiation therapy and chemotherapy. Not all cancers, and not all cervical cancers, are resectable at the time of diagnosis. Tumors such as cervical cancer tumors that are at an advanced stage often require radiotherapy or chemotherapy treatment.

Radiotherapy requires maximized exposure of the affected tissues while sparing normal surrounding tissues. Interstitial therapy, where needles containing a radioactive source are embedded in the tumor, has become a valuable new approach. In this way, large doses of radiation can be delivered locally while sparing the surrounding normal structures. Intraoperative radiotherapy, where the beam is placed directly onto the tumor during surgery while normal structures are moved safely away from the beam, is another specialized radiation technique. Again, this achieves effective irradiation of the tumor while limiting exposure to surrounding structures. Despite the obvious advantage of approaches predicated upon local control of the irradiation, patient survival rate is still very low.

Chemotherapy relies upon a generalized damage to DNA and destabilization of chromosomal structure which eventually leads to destruction of cancer cells. The non-selective nature of these treatments, however, often results in severe and debilitating side effects. The systemic use of these drugs may result in damage to normally healthy organs and tissues, and compromise the long-term health of the patient.

The effects of glucocorticoid receptor ("GR") mediated signaling pathway on cancer cells in general are controversial. On one hand, it is believed that activating the GR signaling pathways advantageously induces apoptosis in malignant lymphoid cancers. See Schlossmacher, J. Endocrino. (2011) 211, 17-25. On the other hand, it has been reported that agents blocking the GR signaling pathway can potentiate chemotherapy in killing breast cancer cells. See U.S. Pat. No. 9,149,485. Mifepristone, a steroidal, non-selective agent that blocks the GR signaling pathway and other steroidal signaling pathways (including progesterone-receptor signaling pathway), has been suggested for treatment of cervical cancer (US Pat. Publ. No. 2004/0102422). However, GR signaling is believed to have the opposite effect in some other cancers. For example, the prevailing view regarding pancreatic cancer is that glucocorticoid, e.g., dexamethasone, can relieve side effects of the chemotherapeutic agent and should be co-administered with chemotherapeutic agents in treating pancreatic cancer. Zhang et al., BMC Cancer, 2006 Mar. 15 6: 61. Further, it has been reported that dexamethasone, a glucocorticoid receptor agonist, inhibits pancreatic cancer cell growth. See, Normal et al., J. Surg. Res. 1994 July; 57(1): 33-8. Thus, the reposts in the literature are often contradictory, and it remains unclear whether or not glucocorticoid signaling will have an effect on a cancer, and whether such an effect may be a positive or a negative effect.

Accordingly, in view of the lack of good treatments options for many cancer patients, improved treatments for cancerous tumors, including cervical cancer, are desired.

SUMMARY

Disclosed herein are novel methods for treating a subject hosting a cancerous tumor, such as a cervical cancer tumor or other cancerous tumor (e.g., breast cancer, ovarian cancer, prostate cancer). The present application provides novel and surprising combination therapies that employ non-steroidal compounds that inhibit GR signaling to treat patients suffering from cancer, including patients suffering from cervical cancer and other cancers. The methods comprise administering to the subject an effective amount of a chemotherapeutic agent and an effective amount of a non-steroidal selective glucocorticoid receptor modulator (SGRM) to reduce the tumor load of the cancerous tumor in the subject. In some cases, the cancerous tumor is a cervical cancer tumor.

In some cases, the chemotherapeutic agent is selected from the group consisting of antimicrotubule agents, alkylating agents, topoisomerase inhibitors, endoplasmic reticulum stress inducing agents, antimetabolites, mitotic inhibitors and combinations thereof. In some cases, the chemotherapeutic agent is a taxane. In some cases, the chemotherapeutic agent is selected from the group consisting of nab-paclitaxel, 5-fluorouracil (5-FU), gemcitabine, cisplatin and capecitabine.

In some cases, the glucocorticoid receptor modulator is orally administered. In some cases, the glucocorticoid receptor modulator is administered by transdermal application, by a nebulized suspension, or by an aerosol spray.

In some cases, the effective amount of the SGRM is a daily dose of between 1 and 100 mg/kg/day, wherein the SGRM is administered with at least one chemotherapeutic agent. In some embodiments, the daily dose of the SGRM is 1, 2, 4, 6, 8, 10, 12, 14, 16, 18, 20, 30, 40, 50 60, 70, 80, 90 or 100 mg/kg/day. In some cases, the glucocorticoid receptor modulator is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

In some cases, the glucocorticoid receptor modulator backbone is a fused azadecalin. In some cases, the fused azadecalin is a compound having the following formula:

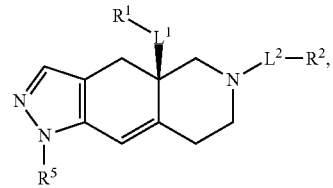

wherein $L^1$ and $L^2$ are members independently selected from a bond and unsubstituted alkylene; $R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$, and —$C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen; $R^2$ has the formula:

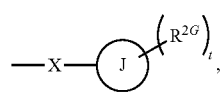

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$; J is phenyl; t is an integer from 0 to 5; X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

In some cases, the fused azadecalin is

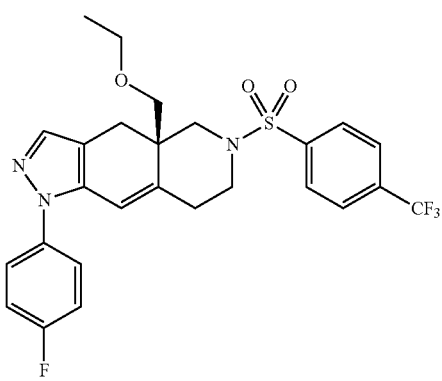 [SMILES: CCOC[C@]12Cc3cnn(-c4ccc(F)cc4)c3C=C1CCN(S(=O)(=O)c1ccc(C(F)(F)F)cc1)C2]

In some cases, the glucocorticoid receptor modulator backbone is a heteroaryl ketone fused azadecalin or an octahydro fused azadecalin. In some cases, the heteroaryl ketone fused azadecalin has the formula:

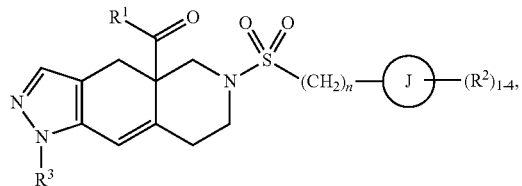

wherein $R^1$ is a heteroaryl ring having from 5 to 6 ring members and from 1 to 4 heteroatoms each independently selected from the group consisting of N, O, and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl; ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2C}$ groups; alternatively, two $R^2$ groups linked to the same carbon are combined to form an oxo group (=O); alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups; $R^{2a}$ and $R^{2b}$ are each independently selected from the group consisting of hydrogen and $C_{1-6}$ alkyl; each $R^{2C}$ is independently selected from the group consisting of hydrogen, halogen, hydroxy, $C_{1-6}$ alkoxy, $C_{1-6}$ haloalkoxy, CN, and $NR^{2a}R^{2b}$; each $R^{2d}$ is independently selected from the group consisting of hydrogen and $C_{1-6}$ alkyl, or two $R^{2d}$ groups attached to the same ring atom are combined to form (=O); $R^3$ is selected from the group consisting of phenyl and pyridyl, each optionally substituted with 1-4 $R^{3a}$ groups; each $R^{3a}$ is independently selected from the group consisting of hydrogen, halogen, and $C_{1-6}$ haloalkyl; and subscript n is an integer from 0 to 3; or salts and isomers thereof.

In some cases, the heteroaryl-ketone fused azadecalin is

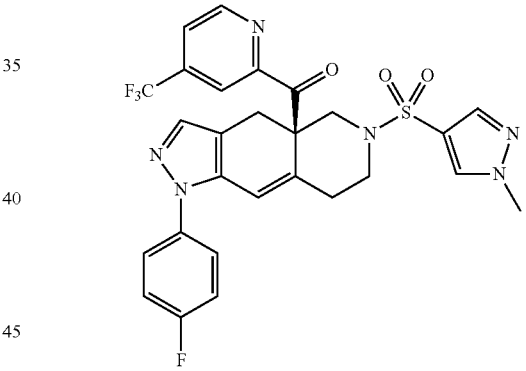

In some cases, the octahydro fused azadecalin has the formula:

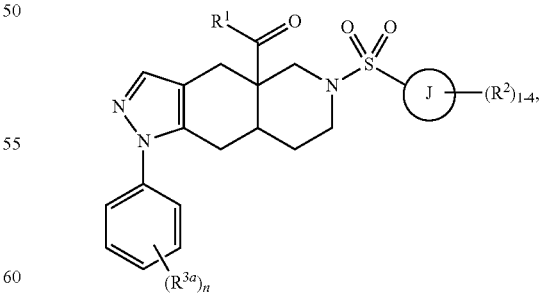

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of an aryl ring and a heteroaryl ring having from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S; alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups; $R^{2a}$, $R^{2b}$ and $R^{2c}$ are each independently selected from the group consisting of hydrogen and $C_{1-6}$ alkyl; each $R^{3a}$ is independently halogen; and subscript n is an integer from 0 to 3, or salts and isomers thereof.

In some cases, the SGRM is CORT125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

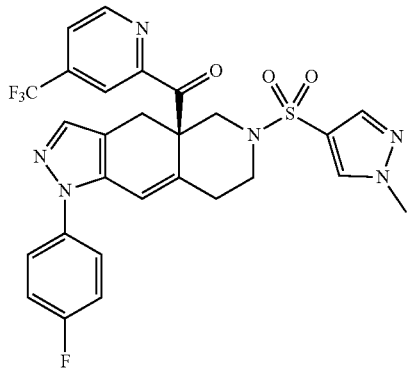 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

In some cases, the SGRM is CORT125281, i.e., ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazol[3,4-g]isoquinolin-4a-yl)(4-(trifluoromethyl)pyridin-2-yl)methanone, which has the following structure:

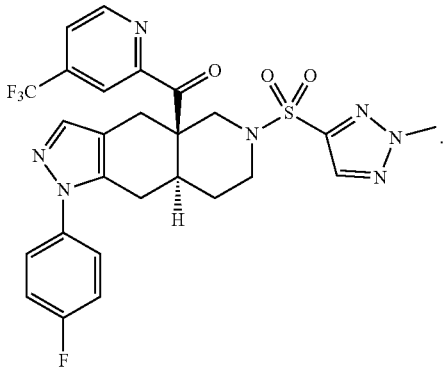 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

DETAILED DESCRIPTION

A. Introduction

Figure 1:
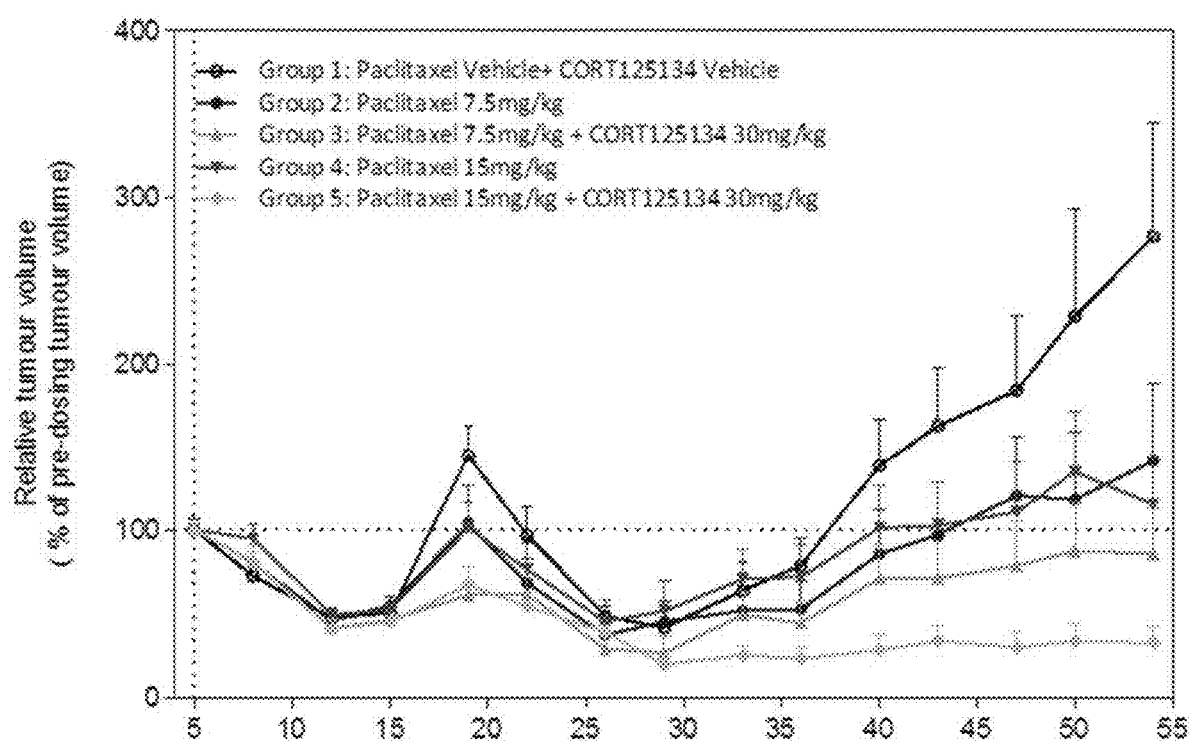
FIG. 1 shows tumor growth data from five groups of mice that were treated with 1) intravenous (i.v.) vehicle; 2) i.v. paclitaxel at 7.5 mg/kg; 3) CORT125134 (30 mg/kg) and paclitaxel (7.5 mg/kg); 4) i.v. paclitaxel at 15 mg/kg; and 5) CORT125134 (30 mg/kg) and paclitaxel (15 mg/kg).

This method disclosed herein can be used to treat a patient hosting a cancerous tumor by administering an effective amount of a SGRM in combination with an effective amount of chemotherapy to reduce the cancerous tumor load. In embodiments, the cancer is cervical cancer. Applicant has discovered that treatments combining a SGRM with a chemotherapeutic agent is more effective than treatments with the therapeutic alone.

B. Definitions

As used herein, the term "tumor" and the term "cancer" are used interchangeably and both refer to an abnormal growth of tissue that results from excessive cell division. A tumor that invades the surrounding tissue and/or can metastasize is referred to as "malignant." A tumor that does not metastasize is referred to as "benign."

As used herein, the term "subject" or "patient" refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a cervical cancer which is being targeted by the compositions and methods of the present invention. In some cases, a subject may suffer from one or more types of cancer simultaneously, at least one of which is a cervical cancer, which is targeted by the compositions and methods of the present invention.

As used herein, the term "cancerous tumor" refers to any solid or semi-solid malignant neoplastic growth.

As used herein, the term "cervical cancer" refers to any tumor in the cervix of a patient, or derived from the cervix of a patient.

As used herein, the term "tumor load" or "tumor burden" generally refers to the number of cancer cells, the size of a tumor, or the amount of cancer in the body in a subject at any given time. Tumor load can be detected by e.g., measuring the expression of tumor specific genetic markers and measuring tumor size by a number of well-known, biochemical or imaging methods disclosed herein, infra.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. The effective amount can be an amount effective to invoke an antitumor response. For the purpose of this disclosure, the effective amount of SGRM or the effective amount of a chemotherapeutic agent is an amount that would reduce tumor load or bring about other desired beneficial clinical outcomes related to cancer improvement when combined with a chemotherapeutic agent or SGRM, respectively.

As used herein, the terms "administer," "administering," "administered" or "administration" refer to providing a compound or a composition (e.g., one described herein), to a subject or patient.

As used herein, the term "combination therapy" refers to the administration of at least two pharmaceutical agents to a subject to treat a disease. The two agents may be administered simultaneously, or sequentially in any order during the entire or portions of the treatment period. The at least two agents may be administered following the same or different dosing regimens. In some cases, one agent is administered following a scheduled regimen while the other agent is administered intermittently. In some cases, both agents are administered intermittently. In some embodiments, the one pharmaceutical agent, e.g., a SGRM, is administered daily, and the other pharmaceutical agent, e.g., a chemotherapeutic agent, is administered every two, three, or four days.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "glucocorticosteroid" ("GC") or "glucocorticoid" refers to a steroid hormone that binds to a glucocorticoid receptor. Glucocorticosteroids are typically characterized by having 21 carbon atoms, an α,β-unsaturated ketone in ring A, and an α-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

As used herein, the term "Glucocorticoid receptor" ("GR") refers to a family of intracellular receptors which specifically bind to cortisol and/or cortisol analogs. The glucocorticoid receptor is also referred to as the cortisol receptor. The term includes isoforms of GR, recombinant GR and mutated GR. "Glucocorticoid receptor" ("GR") refers to the type II GR which specifically binds to cortisol and/or cortisol analogs such as dexamethasone (See, e.g., Turner & Muller, J. Mol. Endocrinol. Oct. 1, 2005 35 283-292).

"Glucocorticoid receptor modulator" refers to any compound which inhibits any biological response associated with the binding of GR to an agonist. For example, a GR agonist, such as dexamethasone, increases the activity of tyrosine aminotransferase (TAT) in HepG2 cells (a human liver hepatocellular carcinoma cell line; ECACC, UK). Accordingly, GR modulators of the present invention can be identified by measuring the ability of the compound to inhibit the effect of dexamethasone. TAT activity can be measured as outlined in the literature by A. Ali et al., J. Med. Chem., 2004, 47, 2441-2452. A modulator is a compound with an $IC_{50}$ (half maximal inhibition concentration) of less than 10 micromolar. See Example 1, infra.

As used herein, the term "selective glucocorticoid receptor modulator" refers to any composition or compound which inhibits any biological response associated with the binding of a GR to an agonist. By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor modulator bind GR with an affinity that is 10× greater ($\frac{1}{10}^{th}$ the $K_d$ value) than its affinity to the MR, AR, or PR, both the MR and PR, both the MR and AR, both the AR and PR, or to the MR, AR, and PR. In a more preferred embodiment, the selective glucocorticoid receptor modulator binds GR with an affinity that is 100× greater ($\frac{1}{100}^{th}$ the $K_d$ value) than its affinity to the MR, AR, or PR, both the MR and PR, both the MR and AR, both the AR and PR, or to the MR, AR, and PR. In another embodiment, the selective glucocorticoid receptor modulator binds GR with an affinity that is 1000× greater ($\frac{1}{1000}^{th}$ the $K_d$ value) than its affinity to the MR, AR, or PR, both the MR and PR, both the MR and AR, both the AR and PR, or to the MR, AR, and PR.

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

As used herein, the phrase "non-steroidal backbone" in the context of SGRMs refers to SGRMs that do not share structural homology to, or are not modifications of, cortisol with its steroid backbone containing seventeen carbon atoms, bonded in four fused rings. Such compounds include synthetic mimetics and analogs of proteins, including partially peptidic, pseudopeptidic and non-peptidic molecular entities.

Non-steroidal SGRM compounds include SGRMs having a fused azadecalin backbone, a heteroaryl ketone fused azadecalin backbone, and an octahydro fused azadecalin backbone. Exemplary glucocorticoid receptor modulators having a fused azadecalin backbone include those described in U.S. Pat. Nos. 7,928,237 and 8,461,172. Exemplary glucocorticoid receptor modulators having a heteroaryl ketone fused azadecalin backbone include those described in U.S. Pat. No. 8,859,774, entitled Heteroaryl-Ketone Fused Azadecalin Glucocorticoid Receptor Modulators. Exemplary glucocorticoid receptor modulators having an octahydro fused azadecalin backbone include those described in U.S. Patent Application Publication No. 2015-0148341 A1, entitled Octahydro Fused Azadecalin Glucocorticoid Receptor Modulators, filed on Nov. 21, 2014.

Where substituent groups are specified by their conventional chemical formulae, written from left to right, they equally encompass the chemically identical substituents that would result from writing the structure from right to left, e.g., —$CH_2O$— is equivalent to —$OCH_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, and $C_{5-6}$. For example, $C_{1-6}$ alkyl includes, but is not limited to, methyl, ethyl, propyl, isopropyl, butyl, isobutyl, sec.butyl, tert.butyl, pentyl, isopentyl, and hexyl.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine, and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$, and include trifluoromethyl, fluoromethyl, etc.

The term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, and perfluoroethoxy.

"Cycloalkyl" refers to a saturated or partially unsaturated, monocyclic, fused bicyclic, or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene, and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to, cyclopropyl, cyclobutyl, cyclopentyl, cyclohexyl, cycloheptyl, and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"Heterocycloalkyl" refers to a saturated ring system having from 3 to 12 ring members and from 1 to 4 heteroatoms of N, O, and S. Additional heteroatoms can also be useful, including but not limited to, B, Al, Si, and P. The heteroatoms can also be oxidized, such as, but not limited to, —S(O)— and —$S(O)_2$—. Heterocycloalkyl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as 6, 7, 8, 9, 10, 11, 12, 13, 14, 15, or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, that has a methylene linking group. Some aryl groups have from 6 to 12 ring members, such as phenyl, naphthyl, or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic, fused bicyclic, or tricyclic aromatic ring assembly containing 5 to 16 ring atoms, where from 1 to 5 of the ring atoms are a heteroatom such as N, O, or S. Additional heteroatoms can also be useful, including but not limited to, B, Al, Si, and P. The heteroatoms can also be oxidized, such as, but not limited to, N-oxide, —S(O)—, and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5; or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4-, and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2-, and 3-pyrrole; pyridine includes 2-, 3- and 4-pyridine; imidazole includes 1-, 2-, 4- and 5-imidazole; pyrazole includes 1-, 3-, 4- and 5-pyrazole; triazole includes 1-, 4- and 5-triazole; tetrazole includes 1- and 5-tetrazole; pyrimidine includes 2-, 4-, 5- and 6-pyrimidine; pyridazine includes 3- and 4-pyridazine; 1,2,3-triazine includes 4- and 5-triazine; 1,2,4-triazine includes 3-, 5- and 6-triazine; 1,3,5-triazine includes 2-triazine; thiophene includes 2- and 3-thiophene; furan includes 2- and 3-furan; thiazole includes 2-, 4- and 5-thiazole; isothiazole includes 3-, 4- and 5-isothiazole; oxazole includes 2-, 4- and 5-oxazole; isoxazole includes 3-, 4- and 5-isoxazole; indole includes 1-, 2- and 3-indole; isoindole includes 1- and 2-isoindole; quinoline includes 2-, 3- and 4-quinoline; isoquinoline includes 1-, 3- and 4-isoquinoline; quinazoline includes 2- and 4-quinoazoline; cinnoline includes 3- and 4-cinnoline; benzothiophene includes 2- and 3-benzothiophene; and benzofuran includes 2- and 3-benzofuran.

Some heteroaryl groups include those having from 5 to 10 ring members and from 1 to 3 ring atoms including N, O, or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S, or N.

"Salt" refers to acid or base salts of the compounds used in the methods of the present invention. Illustrative examples of pharmaceutically-acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically-acceptable salts are non-toxic. Additional information on suitable pharmaceutically-acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to produce compounds which are not inherently unstable—and/or would be known to one of ordinary skill in the art as likely to be unstable under ambient conditions—such as aqueous, neutral, or physiological conditions.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. Non-limiting examples of pharmaceutically-acceptable excipients include water, NaCl, normal saline solutions, lactated Ringer's, normal sucrose, normal glucose, binders, fillers, disintegrants, lubricants, coatings, sweeteners, flavors and colors, and the like. One of ordinary skill in the art will recognize that other pharmaceutical excipients are useful in the present invention.

C. Cervical Tumors

Cervical cancer is a malignant tumor within the cervix, or derived from the cervix. Cervical cancer is the fourth most-common cause of death in women world-wide. In the United States, well over 10,000 new cases are identified each year. Patients suffering from cervical cancer may not experience symptoms during the initial stages of the disease. Risk factors for cervical cancer in women include: history of human papilloma viral (HPV) infection, smoking, and other factors. However, not all patients in the currently recognized risk categories will develop cervical cancers.

Cervical cancer symptoms include abnormal vaginal bleeding and pain in the pelvic area. Cervical cancer may be, for example, a squamous cell carcinoma, and adenocarcinoma, an adenosquamous carcinoma, a small cell carcinoma, a neuroendocrine tumor, or other cancer type.

Visual screening of the cervix, often with the use of visual contrast agents such as acetic acid, is commonly performed during routine patient visits, but the results are not definitive. Although the "Pap smear" test is used to screen for cervical cancer, but negative results from that screening test are often incorrect. Biopsies of cervical tissue may be used to identify or diagnose cervical cancer. One or more of imaging based methods, such as, magnetic resonance imaging (MRI), computed tomography (CT), X-ray, and positron emission tomography (PET) scan, or ultrasonography (US), are often performed on subjects suspected of having cervical cancer, e.g., based on exhibition of the related clinical symptoms. Results from these biopsies or imaging tests are often combined with the patient's medical history, physical examination and lab tests to provide accurate diagnosis as well as information regarding the origin of the tumor.

The presence of cervical cancer, the type and stage of cervical cancer can be confirmed by histological analysis of the tumor performed by a pathologist. Histology dictates many aspects of cervical cancer clinical treatment, management, and prognosis.

D. Cancerous Tumors

The methods disclosed herein are applicable for treating cancerous tumors. After the diagnosis of cervical cancer, the tumor can be evaluated to determine stage and other tumor characteristics.

E. Glucocorticoid Receptor Modulators (GRM)

Generally, treatment of a cancerous tumor can be provided by administering an effective amount of a chemotherapeutic agent in combination with an effective amount of a SGRM of any chemical structure or mechanism of action. Provided herein, are classes of exemplary GRMs and specific members of such classes. However, one of skill in the art will readily recognize other related or unrelated SGRMs that can be employed in the treatment methods described herein.

Non-Steroidal Anti-Glucocorticoid Receptors Modulators

Provided herein, are classes of exemplary non-steroidal glucocorticoid receptor modulators (GRMs) and specific members of such classes that can be used for the method disclosed herein. However, one of skill in the art will readily recognize other related or unrelated glucocorticoid receptor modulators that can be employed in the treatment methods described herein. These include synthetic mimetics and analogs of proteins, including partially peptidic, pseudopeptidic and non-peptidic molecular entities. For example, oligomeric peptidomimetics useful in the invention include ($\alpha$-$\beta$-unsaturated) peptidosulfonamides, N-substituted glycine derivatives, oligo carbamates, oligo urea peptidomimetics, hydrazinopeptides, oligosulfones and the like (See, e.g., Amour, Int. J. Pept. Protein Res. 43:297-304, 1994; de Bont, Bioorganic & Medicinal Chem. 4:667-672, 1996).

Examples of non-steroidal GR modulators include the GR antagonist compounds disclosed in U.S. Pat. Nos. 5,696, 127; 6,570,020; and 6,051,573; the GR antagonist compounds disclosed in US Patent Application 20020077356, the glucocorticoid receptor antagonists disclosed in Bradley et al., J. Med. Chem. 45, 2417-2424 (2002), e.g., 4$\alpha$(S)-benzyl-2(R)-chloroethynyl-1,2,3,4,4$\alpha$,9,10,10$\alpha$(R)-octahydro-phenanthrene-2,7-diol ("CP 394531") and 4$\alpha$(S)-benzyl-2(R)-prop-1-ynyl-1,2,3,4,4$\alpha$,9,10,10$\alpha$(R)-octahydro-phenanthrene-2,7-diol ("CP 409069"); and the compounds disclosed in PCT International Application No. WO 96/19458, which describes non-steroidal compounds which are high-affinity, highly selective antagonists for steroid receptors, such as 6-substituted-1,2-dihydro-N-protected-quinolines.

For additional compounds that can be utilized in the methods of the invention and methods of identifying and making such compounds, see U.S. Pat. No. 4,296,206 (see above); U.S. Pat. No. 4,386,085 (see above); U.S. Pat. Nos. 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1,2-dihydro N-1 protected quinolines.

In some embodiments, the combination therapy for treating cancer involves a GRM having a fused azadecalin backbone, a heteroaryl ketone fused azadecalin backbone, or an octahydro fused azadecalin backbone.

Exemplary GRMs having a fused azadecalin backbone include those described in U.S. Pat. Nos. 7,928,237; 8,461, 172; and 8,557,839 and can be prepared as disclosed therein. These patents are incorporated herein in their entirety. In some cases, the GRM having a fused azadecalin backbone has the following structure:

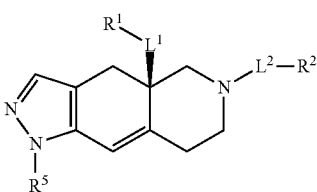

wherein
- $L^1$ and $L^2$ are members independently selected from a bond and unsubstituted alkylene;
- $R^1$ is a member selected from unsubstituted alkyl, unsubstituted heteroalkyl, unsubstituted heterocycloalkyl, $-OR^{1A}$, $-NR^{1C}R^{1D}$, $-C(O)NR^{1C}R^{1D}$, and $-C(O)OR^{1A}$, wherein
  - $R^{1A}$ is a member selected from hydrogen, unsubstituted alkyl and unsubstituted heteroalkyl,
  - $R^{1C}$ and $R^{1D}$ are members independently selected from unsubstituted alkyl and unsubstituted heteroalkyl,
  - wherein $R^{1C}$ and $R^{1D}$ are optionally joined to form an unsubstituted ring with the nitrogen to which they are attached, wherein said ring optionally comprises an additional ring nitrogen;
- $R^2$ has the formula:

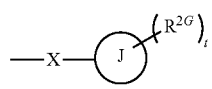

wherein
- $R^{2G}$ is a member selected from hydrogen, halogen, unsubstituted alkyl, unsubstituted heteroalkyl, unsubstituted cycloalkyl, unsubstituted heterocycloalkyl, $-CN$, and $-CF_3$;
- J is phenyl;
- t is an integer from 0 to 5;
- X is $-S(O_2)-$; and
- $R^5$ is phenyl optionally substituted with 1-5 $R^{5A}$ groups, wherein
  - $R^{5A}$ is a member selected from hydrogen, halogen, $-OR^{5A1}$, $-S(O_2)NR^{5A2}R^{5A3}$, $-CN$, and unsubstituted alkyl, wherein
    - $R^{5A1}$ is a member selected from hydrogen and unsubstituted alkyl, and
    - $R^{5A2}$ and $R^{5A3}$ are members independently selected from hydrogen and unsubstituted alkyl,
- or salts and isomers thereof.

Exemplary GRMs having a heteroaryl ketone fused azadecalin backbone include those described in U.S. 2014/0038926, which can be prepared as disclosed therein, and is incorporated herein in its entirety. In some cases, the GRM having a heteroaryl ketone fused azadecalin backbone has the following structure:

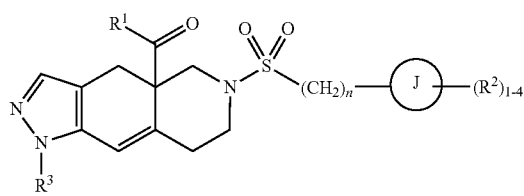

wherein
- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $-CN$, N-oxide, $C_{3-8}$ cycloalkyl, and $C_{3-8}$ heterocycloalkyl;
- ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, $-CN$, $-OH$, $-NR^{2a}R^{2b}$, $-C(O)R^{2a}$, $-C(O)R^{2a}$, $-C(O)NR^{2a}R^{2b}$, $-SR^{2a}$, $-S(O)R^{2a}$, $-S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;
- alternatively, two $R^2$ groups linked to the same carbon are combined to form an oxo group $(=O)$;
- alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;
- $R^{2a}$ and $R^{2b}$ are each independently selected from the group consisting of hydrogen and $C_{1-6}$ alkyl;
- each $R^{2c}$ is independently selected from the group consisting of hydrogen, halogen, hydroxy, $C_{1-6}$ alkoxy, $C_{1-6}$ haloalkoxy, $-CN$, and $-NR^{2a}R^{2b}$;
- each $R^{2d}$ is independently selected from the group consisting of hydrogen and $C_{1-6}$ alkyl, or two $R^{2d}$ groups attached to the same ring atom are combined to form $(=O)$;
- $R^3$ is selected from the group consisting of phenyl and pyridyl, each optionally substituted with 1-4 $R^{3a}$ groups;
- each $R^{3a}$ is independently selected from the group consisting of hydrogen, halogen, and $C_{1-6}$ haloalkyl; and
- subscript n is an integer from 0 to 3;
- or salts and isomers thereof.

Exemplary GRMs having an octahydro fused azadecalin backbone include those described in U.S. Pat. Pub. No. 20150148341 filed on Nov. 21, 2014 and can be prepared as described therein. The disclosure of U.S. Pat. Pub. No. 20150148341 is incorporated herein in their entirety. In some cases, the GRM having an octahydro fused azadecalin backbone has the following structure:

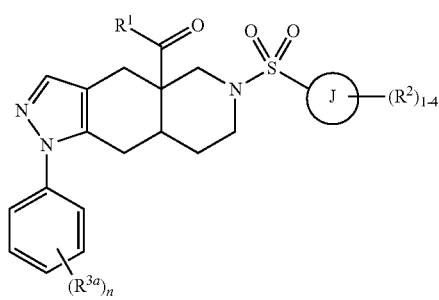

wherein
- $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
- each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;
- ring J is selected from the group consisting of an aryl ring and a heteroaryl ring having from 5 to 6 ring members and from 1 to 4 heteroatoms each independently selected from the group consisting of N, O and S;
- each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)R^{2a}$, —$C(O)NR^{2a}R^{2b}$, —$SR^{2a}$, —$S(O)R^{2a}$, —$S(O)_2 R^{2a}$, $C_{3-8}$ cycloalkyl, and $C_{3-8}$ heterocycloalkyl having from 1 to 3 heteroatoms each independently selected from the group consisting of N, O and S;
- alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;
- $R^{2a}$, $R^{2b}$ and $R^{2c}$ are each independently selected from the group consisting of hydrogen and $C_{1-6}$ alkyl;
- each $R^{3a}$ is independently halogen; and
- subscript n is an integer from 0 to 3;
- or salts and isomers thereof.

F. Identifying Selective Glucocorticoid Receptor Modulators (SGRMS)

To determine whether a test compound is a SGRM, the compound is first subjected to assays to measure its ability to bind to the GR and inhibit GR-mediated activities, which determines whether the compound is a glucocorticoid receptor modulator. The compound, if confirmed to be a glucocorticoid receptor modulator, is then subjected to a selectivity test to determine whether the compound can bind specifically to GR as compared to non GR proteins, such as the estrogen receptor, the progesterone receptor, the androgen receptor, or the mineralocorticoid receptor. In one embodiment, a SGRM binds to GR at a substantially higher affinity, e.g., at least 10 times higher affinity, than to non-GR proteins. A SGRM may exhibit a 100 fold, 1000 fold or greater selectivity for binding to GR relative to binding to non GR proteins.

i. Binding

A test compounds' ability to bind to the glucocorticoid receptor can be measured using a variety of assays, for example, by screening for the ability of the test compound to compete with a glucocorticoid receptor ligand, such as dexamethasone, for binding to the glucocorticoid receptor. Those of skill in the art will recognize that there are a number of ways to perform such competitive binding assays. In some embodiments, the glucocorticoid receptor is pre-incubated with a labeled glucocorticoid receptor ligand and then contacted with a test compound. This type of competitive binding assay may also be referred to herein as a binding displacement assay. A decrease of the quantity of labeled ligand bound to glucocorticoid receptor indicates that the test compound binds to the glucocorticoid receptor. In some cases, the labeled ligand is a fluorescently labeled compound (e.g., a fluorescently labeled steroid or steroid analog). Alternatively, the binding of a test compound to the glucocorticoid receptor can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a glucocorticoid receptor ligand and the binding agent can be glucocorticoid receptor bound to a solid phase. Alternatively, the labeled analyte can be labeled glucocorticoid receptor and the binding agent can be a solid phase glucocorticoid receptor ligand. The concentration of labeled analyte bound to the capture agent is inversely proportional to the ability of a test compound to compete in the binding assay.

Alternatively, the competitive binding assay may be conducted in the liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the glucocorticoid receptor may be altered by the binding of the glucocorticoid receptor to its ligand or test compound. This alteration in the labeled glucocorticoid receptor results in a decrease or increase in the signal emitted by label, so that measurement of the label at the end of the binding assay allows for detection or quantitation of the glucocorticoid receptor in the bound state. A wide variety of labels may be used. The component may be labeled by any one of several methods. Useful radioactive labels include those incorporating $^3H$, $^{125}I$, $^{35}S$, $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art. In some cases, a test compound is contacted with a GR in the presence of a fluorescently labeled ligand (e.g., a steroid or steroid analog) with a known affinity for the GR, and the quantity of bound and free labeled ligand is estimated by measuring the fluorescence polarization of the labeled ligand.

ii. Activity

1) HepG2 Tyrosine Aminotransferase (TAT) Assay

Compounds that have demonstrated the desired binding affinity to GR are tested for their activity in inhibiting GR mediated activities. The compounds are typically subject to a Tyrosine Aminotransferase Assay (TAT assay), which assesses the ability of a test compound to inhibit the induction of tyrosine aminotransferase activity by dexamethasone. See Example 1. GR modulators that are suitable for the method disclosed herein have an $IC_{50}$ (half maximal inhibition concentration) of less than 10 micromolar. Other assays, including but not limited to those described below, can also be deployed to confirm the GR modulation activity of the compounds.

2) Cell-Based Assays

Cell-based assays which involve whole cells or cell fractions containing glucocorticoid receptors can also be used to assay for a test compound's binding or modulation of activity of the glucocorticoid receptor. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemia cells, Burkitt's lymphoma cells, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, the glucocorticoid receptor can be expressed in cells that do not express an endogenous version of the glucocorticoid receptor.

In some cases, fragments of the glucocorticoid receptor, as well as protein fusions, can be used for screening. When molecules that compete for binding with the glucocorticoid receptor ligands are desired, the GR fragments used are fragments capable of binding the ligands (e.g., dexamethasone). Alternatively, any fragment of GR can be used as a target to identify molecules that bind the glucocorticoid receptor. Glucocorticoid receptor fragments can include any fragment of, e.g., at least 20, 30, 40, 50 amino acids up to a protein containing all but one amino acid of glucocorticoid receptor.

In some embodiments, a reduction in signaling triggered by glucocorticoid receptor activation is used to identify glucocorticoid receptor modulators. Signaling activity of the glucocorticoid receptor can be determined in many ways. For example, downstream molecular events can be monitored to determine signaling activity. Downstream events include those activities or manifestations that occur as a result of stimulation of a glucocorticoid receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g., the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Compounds that are tested in whole-cell assays can also be tested in a cytotoxicity assay. Cytotoxicity assays are used to determine the extent to which a perceived effect is due to non-glucocorticoid receptor binding cellular effects. In an exemplary embodiment, the cytotoxicity assay includes contacting a constitutively active cell with the test compound. Any decrease in cellular activity indicates a cytotoxic effect.

3) Additional Assays

Further illustrative of the many assays which can be used to identify compositions utilized in the methods of the invention, are assays based on glucocorticoid activities in vivo. For example, assays that assess the ability of a putative GR modulator to inhibit uptake of 3H-thymidine into DNA in cells which are stimulated by glucocorticoids can be used. Alternatively, the putative GR modulator can complete with 3H-dexamethasone for binding to a hepatoma tissue culture GR (see, e.g., Choi, et al., *Steroids* 57:313-318, 1992). As another example, the ability of a putative GR modulator to block nuclear binding of 3H-dexamethasone-GR complex can be used (Alexandrova et al., *J. Steroid Biochem. Mol. Biol.* 41:723-725, 1992). To further identify putative GR modulators, kinetic assays able to discriminate between glucocorticoid agonists and modulators by means of receptor-binding kinetics can also be used (as described in Jones, *Biochem J.* 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR modulator) at varying concentrations. $^{3}$H-uridine is added to the cell culture, which is further incubated, and the extent of incorporation of radiolabel into polynucleotide is measured. Glucocorticoid agonists decrease the amount of $^{3}$H-uridine incorporated. Thus, a GR modulator will oppose this effect.

iii. Selectivity

The GR modulators selected above are then subject to a selectivity assay to determine whether they are SGRMs.

Typically, selectivity assays include testing a compound that binds glucocorticoid receptor in vitro for the degree of binding to non-glucocorticoid receptor proteins. Selectivity assays may be performed in vitro or in cell based systems, as described above. Binding may be tested against any appropriate non-glucocorticoid receptor protein, including antibodies, receptors, enzymes, and the like. In an exemplary embodiment, the non-glucocorticoid receptor binding protein is a cell-surface receptor or nuclear receptor. In another exemplary embodiment, the non-glucocorticoid receptor protein is a steroid receptor, such as estrogen receptor, progesterone receptor, androgen receptor, or mineralocorticoid receptor.

The selectivity of the antagonist for the GR relative to the MR can be measured using a variety of assays known to those of skill in the art. For example, specific antagonists can be identified by measuring the ability of the antagonist to bind to the GR compared to the MR (see, e.g., U.S. Pat. Nos. 5,606,021; 5,696,127; 5,215,916; 5,071,773). Such an analysis can be performed using either a direct binding assay or by assessing competitive binding to the purified GR or MR in the presence of a known ligand. In an exemplary assay, cells that stably express the glucocorticoid receptor or mineralocorticoid receptor (see, e.g., U.S. Pat. No. 5,606,021) at high levels are used as a source of purified receptor. The affinity of the ligand for the receptor is then directly measured. Those GR modulators that exhibit at least a 10 fold, 100-fold higher affinity, often 1000-fold, for the GR relative to the MR are then selected for use in the methods of the invention.

The selectivity assay may also include assaying the ability to inhibit GR-mediated activities, but not MR-mediated activities. One method of identifying such a GR-specific modulator is to assess the ability of an antagonist to prevent activation of reporter constructs using transfection assays (see, e.g., Bocquel et al, J. Steroid Biochem Molec. Biol. 45:205-215, 1993; U.S. Pat. Nos. 5,606,021, 5,929,058). In an exemplary transfection assay, an expression plasmid encoding the receptor and a reporter plasmid containing a reporter gene linked to receptor-specific regulatory elements are cotransfected into suitable receptor-negative host cells. The transfected host cells are then cultured in the presence and absence of a hormone, such as cortisol or an analog thereof, able to activate the hormone responsive promoter/enhancer element of the reporter plasmid. Next the transfected and cultured host cells are monitored for induction (i.e., the presence) of the product of the reporter gene sequence. Finally, the expression and/or steroid binding-capacity of the hormone receptor protein (coded for by the receptor DNA sequence on the expression plasmid and produced in the transfected and cultured host cells), is measured by determining the activity of the reporter gene in the presence and absence of an antagonist. The antagonist activity of a compound may be determined in comparison to known antagonists of the GR and MR receptors (see, e.g., U.S. Pat. No. 5,696,127). Efficacy is then reported as the percent maximal response observed for each compound relative to a reference antagonist compound. GR modulators that exhibits at least a 100-fold, often 1000-fold or greater, activity towards the GR relative to the MR, PR, or AR are then selected for use in the methods disclosed herein.

An exemplar SGRM that can be used in the methods disclosed herein is CORT 108297, i.e., (R)-(4a-ethoxymethyl-1-(4-fluorophenyl)-6-(4-trifluoromethyl-benzenesulfonyl)-4,4a,5,6,7,8-hexahydro-1H,1,2,6-triaza-cyclopenta[b]naphthalene, which has the following structure:

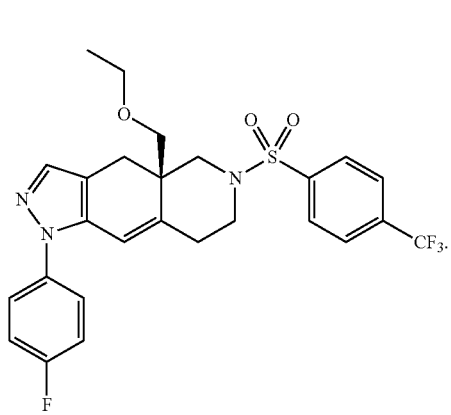 [SMILES: CCOC[C@]12Cc3cnn(-c4ccc(F)cc4)c3C=C1CCN(S(=O)(=O)c1ccc(C(F)(F)F)cc1)C2]

An exemplar SGRM that can be used in the methods disclosed herein is CORT 125134, i.e., (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

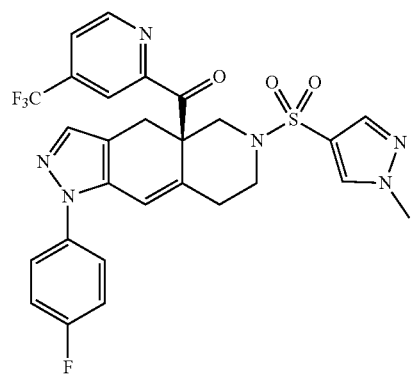 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Another exemplar SGRM that can be used in the methods disclosed herein is CORT125281, i.e., ((4aR,8aS)-1-(4-fluorophenyl)-6-(2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, which has the following structure:

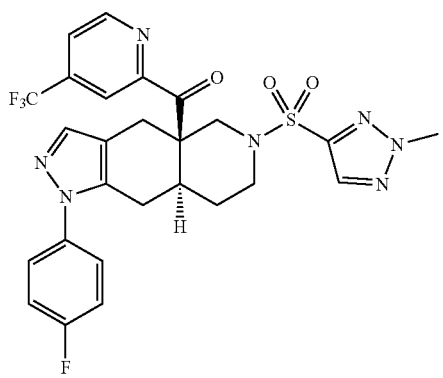 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

G. Pharmaceutical Compositions and Administration

In some embodiments, the present invention provides a pharmaceutical composition including a pharmaceutically acceptable excipient and a SGRM.

SGRMs can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. SGRMs can also be administered by injection, that is, intravenously, intramuscularly, intracutaneously, subcutaneously, intraduodenally, or intraperitoneally. Also, SGRMs can be administered by inhalation, for example, intranasally. Additionally, SGRMs can be administered transdermally. Accordingly, the present invention also provides pharmaceutical compositions including a pharmaceutically acceptable carrier or excipient and a SGRM.

For preparing pharmaceutical compositions from SGRMs, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component, a SGRM. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a SGRM in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

SGRMs can be delivered by transdermally, by a topical route, formulated as applicator sticks, solutions, suspensions, emulsions, gels, creams, ointments, pastes, jellies, paints, powders, and aerosols.

SGRMs can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component, a GRM. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 6000 mg, most typically 50 mg to 500 mg. Suitable dosages also include about 1 mg, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents.

Single or multiple administrations of formulations can be administered depending on the dosage and frequency as required and tolerated by the patient. The formulations should provide a sufficient quantity of active agent to effectively treat the disease state. Thus, in one embodiment, the pharmaceutical formulation for oral administration of a GRM is in a daily amount of between about 0.01 to about 150 mg per kilogram of body weight per day (mg/kg/day). In some embodiments, the daily amount is from about 1.0 to 100 mg/kg/day, 5 to 50 mg/kg/day, 10 to 30 mg/kg/day, and 10 to 20 mg/kg/day. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

The duration of treatment with SGRM to reduce the tumor load of cancerous tumor or otherwise ameliorate the symptoms of the tumor can vary according to the severity of the condition in a subject and the subject's response to SGRMs. In some embodiments, SGRMs can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. Generally administration of a SGRM should be continued until clinically significant reduction or amelioration is observed. Treatment with the SGRM in accordance with the invention may last for as long as two years or even longer.

In some embodiments, administration of a SGRM is not continuous and can be stopped for one or more periods of time, followed by one or more periods of time where administration resumes. Suitable periods where administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

The dosage regimen also takes into consideration pharmacokinetics parameters well known in the art, i.e., the rate of absorption, bioavailability, metabolism, clearance, and the like (see, e.g., Hidalgo-Aragones (1996) *J Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

SGRMs can be used in combination with other active agents known to be useful in modulating a glucocorticoid receptor, or with adjunctive agents that may not be effective alone, but may contribute to the efficacy of the active agent.

In some embodiments, co-administration includes administering one active agent, a SGRM, within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a GR modulator of the invention has been formulated in an acceptable carrier, it can be placed in an appropriate container and labeled for treatment of an indicated condition. For administration of a SGRM, such labeling would include, e.g., instructions concerning the amount, frequency and method of administration.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

H. Chemotherapeutic Agents

Chemotherapeutic agents suitable for use in combination with the SGRM of the invention include agents that have the property of killing cancer cells or inhibiting cancer cell growth, such as those disclosed in US Pat. Pub. No. 20150218274, and also http://chemocare.com/chemotherapy/what-is-chemotherapy/types-of-chemotherapy-.aspx. These agents include, but are not limited to antimicrotubule agents (e.g., taxanes and vinca alkaloids), topoisomerase inhibitors and antimetabolites (e.g., nucleoside analogs acting as such, for example, Gemcitabine), mitotic inhibitors, alkylating agents, antimetabolites, antitumor antibiotics, mitotic inhibitors, anthracyclines, intercalating agents, agents capable of interfering with a signal transduction pathway, agents that promote apoptosis, proteosome inhibitors, and alike.

Alkylating agents are most active in the resting phase of the cell. These types of drugs are cell-cycle non-specific. Exemplary alkylating agents that can be used in combination with the SGRM of the invention include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Antitumor antibiotics are chemo agents obtained from natural products produced by species of the soil fungus Streptomyces. These drugs act during multiple phases of the cell cycle and are considered cell-cycle specific. There are several types of antitumor antibiotics, including but are not limited to Anthracyclines (e.g., Doxorubicin, Daunorubicin, Epirubicin, Mitoxantrone, and Idarubicin), Chromomycins (e.g., Dactinomycin and Plicamycin), Mitomycin and Bleomycin.

Antimetabolites are types of chemotherapy treatments that are cell-cycle specific. When the cells incorporate these antimetabolite substances into the cellular metabolism, they are unable to divide. These class of chemotherapy agents include folic acid antagonists such as Methotrexate; pyrimidine antagonists such as 5-Fluorouracil, Foxuridine, Cytarabine, Capecitabine, and Gemcitabine; purine antagonists such as 6-Mercaptopurine and 6-Thioguanine; Adenosine deaminase inhibitors such as Cladribine, Fludarabine, Nelarabine and Pentostatin.

Exemplary anthracyclines that can be used in combination with the SGRM of the invention include, e.g., doxorubicin (Adriamycin® and Rubex®); Bleomycin (Lenoxane®); Daunorubicin (dauorubicin hydrochloride, daunomycin, and rubidomycin hydrochloride, Cerubidine®); Daunorubicin liposomal (daunorubicin citrate liposome, DaunoXome®); Mitoxantrone (DHAD, Novantrone®); Epirubicin (Ellence); Idarubicin (Idamycin®, Idamycin PFS®); Mitomycin C (Mutamycin®); Geldanamycin; Herbimycin; Ravidomycin; and Desacetylravidomycin.

Antimicrotubule agents include vinca alkaloids and taxanes. Exemplary vinca alkaloids that can be used in combination with the SGRM of the invention include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary taxanes that can be used in combination with the SGRM of the invention include, but are not limited to paclitaxel and docetaxel. Non-limiting examples of paclitaxel agents include nanoparticle albumin-bound paclitaxel ("nab-paclitaxel", marketed as ABRAXANE by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., Bioorganic & Medicinal Chemistry Letters (2007) 17:617-620).

Exemplary proteosome inhibitors that can be used in combination with the SGRM of the invention, include, but are not limited to, Bortezomib (Velcade®); Carfilzomib (PX-171-007, (S)-4-Methyl-N—((S)-1-((((S)-4-methyl-1-((R)-2-methyloxiran-2-yl)-1-oxope-ntan-2-yl)amino)-1-oxo-3-phenylpropan-2-yl)-2-((S)-2-(2-morpholinoacet-amid-o)-4-phenylbutanamido)-pentanamide); marizomib (NPI-0052); ixazomib citrate (MLN-9708); delanzomib (CEP-18770); and O-Methyl-N-[(2-methyl-5-thiazolyl)car-bonyl]-L-seryl-O-methyl-N-[(1S)-2-[(-2R)-2-methyl-2-oxi-ranyl]-2-oxo-1-(phenylmethyl)ethyl]-L-serinamide (ONX-0912).

In some embodiments, the chemotherapeutic agent is selected from the group consisting of chlorambucil, cyclophosphamide, ifosfamide, melphalan, streptozocin, carmustine, lomustine, bendamustine, uramustine, estramustine, carmustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, campothecin, topotecan, 9-nitrocamptothecin, 9-aminocamptothecin, rubifen, gimatecan, diflomotecan, BN80927, DX-895 If, MAG-CPT, amsacrine, etoposide, etoposide phosphate, teniposide, doxorubicin, paclitaxel, docetaxel, gemcitabine, accatin III, 10-deacetyltaxol, 7-xy-losyl-10-deacetyltaxol, cephalomannine, 10-deacetyl-7-epi-taxol, 7-epitaxol, 10-deacetylbaccatin III, 10-deacetyl cephalomannine, gemcitabine, Irinotecan, albumin-bound paclitaxel, Oxaliplatin, Capecitabine, Cisplatin, docetaxel, irinotecan liposome, and etoposide, and combinations thereof.

In certain embodiments, the chemotherapeutic agent is administered at a dose and a schedule that may be guided by doses and schedules approved by the U.S. Food and Drug Administration (FDA) or other regulatory body, subject to empirical optimization. In some cases, the chemotherapeutic agent is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from, e.g. every week, every five days, every four days, every other day to daily, twice, or three times a day. In one embodiment, the chemotherapeutic agent is administered at an oral dose or an intravenous dose from about 100 mg to 600 mg daily, e.g., about 100 mg, 200 mg, 260 mg, 300 mg, 400 mg, or 600 mg daily, every other day or every four days for the whole or a portion of the treatment period. In some embodiments, the chemotherapeutic agent is a taxane and can be used at any standard dose, for example those approved by the FDA, in accordance with the methods of the invention. In various embodiments, the taxane is nab-paclitaxel, which is administered at a dose ranging from 80 mg to 125 mg per square meter of body-surface area as an intravenous infusion over 30 minutes on days 1, 8, and 15 of every 28-day cycle.

In still further embodiments, more than one chemotherapeutic agent may be administered simultaneously, or sequentially in any order during the entire or portions of the treatment period. The two agents may be administered following the same or different dosing regimens.

I. Combination Therapies

Various combinations with a SGRM and a chemotherapeutic agent (or a combination of such agents and compounds) may be employed to reduce the tumor load in the patient. By "combination therapy" or "in combination with", it is not intended to imply that the therapeutic agents must be administered at the same time and/or formulated for delivery together, although these methods of delivery are within the scope described herein. The SGRM and the chemotherapeutic agent can be administered following the same or different dosing regimen. In some embodiments, the SGRM and the chemotherapeutic agent is administered sequentially in any order during the entire or portions of the treatment period. In some embodiments, the SGRM and the anticancer agent is administered simultaneously or approximately simultaneously (e.g., within about 1, 5, 10, 15, 20, or 30 minutes of each other). Non-limiting examples of combination therapies are as follows, with administration of the SGRM and the chemo agent for example, SGRM is "A" and the anticancer agent or compound, given as part of an chemo therapy regime, is "B":

A/B/ AB/A/BB/B/AA/A/BA/B/BB/A/AA/B/B/B B/A/B/B
　　　 B/B/B/A　 B/B/A/B　 A/A/B/B　 A/B/A/B　 A/B/B/A
B/B/A/A
　　　 B/A/B/A　 B/A/A/B　 A/A/A/B　 B/A/A/A　 A/B/A/A
A/A/B/A

Administration of the therapeutic compounds or agents to a patient will follow general protocols for the administration of such compounds, taking into account the toxicity, if any, of the therapy. Surgical intervention may also be applied in combination with the descirbed therapy.

The present methods involvincan be combined with other means of treatment such as surgery, radiation, targeted therapy, immunotherapy, use of growth factor inhibitors, or anti-angiogenesis factors.

J. Evaluate Improvements in Reducing Tumor Loads

The SGRM therapy disclosed herein can reduce the tumor load and confer beneficial clinical outcome to patients having a cancerous tumor. Methods for measuring these responses are well-known to skilled artisans in the field of cancer therapy, e.g., as described in the Response Evaluation Criteria in Solid Tumors ("RECIST") guidelines, available at ctep.cancer.gov/protocolDevelopment/docs/recist_guideline.pdf.

In one approach, the tumor load is measured by assaying expression of tumor-specific biomarkers. This approach is especially useful for metastatic tumors. A tumor-specific biomarker is a protein or other molecule that is unique to cancer cells or is much more abundant in them as compared to non-cancer cells. Biomarkers believed to be useful for identifying cervical cancer include, for example, alpha actinin-4, pyruvate kinase isozyme M1/M2, and others (see, e.g., Van Raemdonck et al., PLoS One September 2014, http://dx.doi.org/10.1371/jounal.pone.0160488).

Methods of measuring the expression levels of a tumor-specific genetic marker are well known. In some embodiments, mRNA of the genentic marker is isolated from the blood sample or a tumor tissue and real-time reverse transcriptase-polymerase chain reaction (RT-PCR) is performed to quantify expression of the genetic marker. In some embodiments, western blots or immunohistochemistry analysis are performed to evaluate the protein expression of the tumor-specific genetic marker. Typically the levels of the tumor-specific genetic marker are measured in multiple samples taken over time of the combination therapy of the invention, and a decrease in levels correlates with a reduction in tumor load.

In another approach, the reduction of tumor load by the combination therapy disclosed herein is shown by a reduction in tumor size or a reduction of amount of cancer in the body. Measuring tumor size is typically achieved by imaging-based techniques. For example, computed tomography (CT) scan can provide accurate and reliable anatomic information about not only tumor shrinkage or growth but also progression of disease by identifying either growth in existing lesions or the development of new lesions or tumor metastasis.

In yet another approach, a reduction of tumor load can be assessed by functional and metabolic imaging techniques. These techniques can provide earlier assessment of therapy response by observing alterations in perfusion, oxygenation and metabolism. For example, $^{18}$F-FDG PET uses radiolabelled glucose analogue molecules to assess tissue metabolism. Tumors typically have an elevated uptake of glucose, a change in value corresponding to a decrease in tumor tissue metabolism indicates a reduction in tumor load. Similar imaging techniques are disclosed in Kang et al., Korean J. Radiol. (2012) 13(4) 371-390.

A patient receiving the therapy disclosed herein may exhibit varying degrees of tumor load reduction. In some cases, a patient can exhibit a Complete Response (CR), also referred to as "no evidence of disease (NED)". CR means all detectable tumor has disappeared as indicated by tests, physical exams and scans. In some cases, a patient receiving the combination therapy disclosed herein can experience a Partial Response (PR), which roughly corresponds to at least a 50% decrease in the total tumor volume but with evidence of some residual disease still remaining. In some cases the residual disease in a deep partial response may actually be dead tumor or scar so that a few patients classified as having a PR may actually have a CR. Also many patients who show shrinkage during treatment show further shrinkage with continued treatment and may achieve a CR. In some cases, a patient receiving the combination therapy can experience a Minor Response (MR), which roughtly means a small amount of shrinkage that is more than 25% of total tumor volume but less than the 50% that would make it a PR. In some cases, a patient receiving the combination therapy can exhibit Stable Disease (SD), which means the tumors stay roughly the same size, but can include either a small amount of growth (typically less than 20 or 25%) or a small amount of shrinkage (Anything less than a PR unless minor responses are broken out. If so, then SD is defined as typically less 25%).

Desired beneficial or desired clinical results from the combination therapy may also include e. g., reduced (i.e., slowing to some extent and/or stop) cancer cell infiltration into peripheral organs; inhibited (i.e., slowing to some extent and/or stop) tumor metastasis; increased response rates (RR); increased duration of response; relieved to some extent one or more of the symptoms associated with the cancer; decreased dose of other medications required to treat the disease; delayed progression of the disease; and/or prolonged survival of patients and/or improved quality of life. Methods for evaluating these effects are well known and/or disclosed in, e.g., cancerguide.org/endpoints.html and RECIST guidelines, supra.

All publications and patent applications cited in this specification are hereby incorporated by reference herein in their entireties as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1. HEPG2 Tyrosine Aminotransferase (Tat) Assay

The following protocol describes an assay for measuring induction of TAT by dexamethasone in HepG2 cells (a human liver hepatocellular carcinoma cell line; ECACC, UK). HepG2 cells are cultured using MEME media supplemented with 10% (v/v) foetal bovine serum; 2 mM L-glutamine and 1% (v/v) NEAA at 37° C., 5%/95% (v/v) $CO_2$/air. The HepG2 cells are then be counted and adjusted to yield a density of 0.125×10$^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% CO$_2$ for 24 hours.

Growth media are then removed and replaced with assay media {RPMI 1640 without phenol red, 2 mM L-glutamine+ 10 µM forskolin}. Test compounds are then be screened against a challenge of 100 nM dexamethasone. Compounds are then be serially half log diluted in 100% (v/v) dimethylsupfoxide from a 10 mM stock. Then an 8-point half-log dilution curve are generated followed by a 1:100 dilution into assay media to give a 10× final assay of the compound concentration, this results in final assay of the compound concentration that ranged 10 to 0.003 µM in 0.1% (v/v) dimethylsulfoxide.

Test compounds are pre-incubated with cells in microtitre plates for 30 minutes at 37° C., 5/95 (v/v) CO$_2$/air, before the addition of 100 nM dexamethasone and then subsequently for 20 hours to allow optimal TAT induction.

HepG2 cells are then lysed with 30 µl of cell lysis buffer containing a protease inhibitor cocktail for 15 minutes at 4° C. 155 µl of substrate mixture can then be added containing 5.4 mM Tyrosine sodium salt, 10.8 mM alpha ketoglutarate and 0.06 mM pyridoxal 5' phosphate in 0.1 M potassium phosphate buffer (pH 7.4). After 2 hours incubation at 37° C. the reaction can be terminated by the addition of 15 µl of 10 M aqueous potassium hydroxide solution, and the plates incubated for a further 30 minutes at 37° C. The TAT activity product can be measured by absorbance at λ 340 nm.

IC$_{50}$ values can be calculated by plotting % inhibition (normalised to 100 nM dexamethasone TAT stimulation) v. compound concentration and fitting the data to a 4 parameter logistic equation. IC$_{50}$ values can converted to Ki (equilibrium dissociation constant) using the Cheng and Prusoff equation, assuming the antagonists were competitive inhibitors with respect to dexamethasone.

Example 2. Reducing Implanted Cervical Cancer Tumor Growth in Mice Using the Combination Therapy of CORT125134 and Paclitaxel Suspensions of human HeLa cervical cancer cells were injected subcutaneously into the right flank of 5-6 week old immunosuppressed female mice (BALB/c nude), five million cells per mouse. Tumors were allowed to grow until they reached a volume of 100-200 mm$^3$. Mice were then grouped into five groups, ten (10) per group. Group 1 was dosed with the paclitaxel vehicle (sterile saline) intravenously (i.v.) every 4 days and the CORT125134 vehicle orally (p.o.) (10% DMSO, 0.1% Tween 80 and 89.9% HPMC (0.5%), 10 ml/kg) every 4 days. Group 2 was dosed with paclitaxel (7.5 mg/kg) i.v. every 4 days. Group 3 was dosed with paclitaxel i.v. every 4 days and with CORT125134 (30 mg/kg) p.o. the day before the administration of paclitaxel and the same day as the administration of paclitaxel. Group 4 received paclitaxel (15 mg/kg) i.v. every 4 days. Group 5 received paclitaxel (15 mg/kg) i.v. every 4 days and CORT125134 (30 mg/kg) p.o. the day before and the day of paclitaxel (15 mg/kg) i.v. administration.

The longest (L) and shortest (S) diameters of the tumors were measured three times a week with electronic calipers and tumor volume was calculated using the formula for an ellipsoid sphere: $S^2 \times L \times (0.5)$. The tumor growth data are shown in FIG. 1, in which the mean tumor volume for each group of mice is plotted against the number of days of tumor growth since initiation of the treatment. Table 1 provides a summary of the results. All treatments provide benefit compared to vehicle alone. The combination of paclitaxel and CORT125134 is more effective than paclitaxel alone, for either dose of paclitaxel.

TABLE 1

| Comparison | p |
| --- | --- |
| Group 1 vs Group 2 | 0.0281 |
| Group 1 vs Group 4 | 0.0006 |
| Group 2 vs Group 3 | 0.008 |
| Group 4 vs Group 5 | <0.0001 |
| Group 3 vs Group 5 | 0.0009 |

Figure 2:
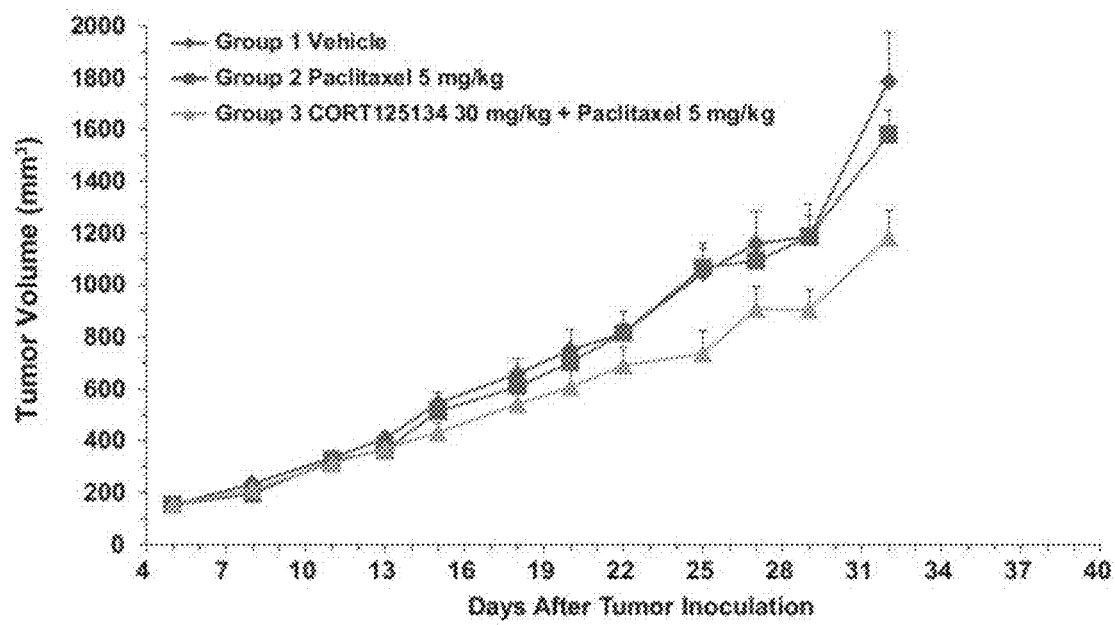
FIG. 2 shows the effect of CORT125134 in combination with paclitaxel in a triple negative breast cancer (TNBC) mouse xenograft model. 10 mice per group, CORT125134 administered orally every day, intravenous paclitaxel administered every 4 days. Data represent mean+SEM.

Example 2. Treating Triple-Negative Breast Cancer Explants with CORT125134 in Combination with Paclitaxel MDA-MB-231 cells (10 million cells per mouse) were injected orthotopically in the right mammary fat pad in groups of female Balb/c nude mice. When the tumors reached a volume of 100-200 mm3, the mice were randomized into groups of 10 and treatment was initiated. Mice were treated as follows: group 1 received vehicle daily, group 2 received paclitaxel 5 mg/kg i.v. every 4 days, group 3 received paclitaxel 5 mg/kg i.v. every 4 days and CORT125134 30 mg/kg p.o. daily. Tumor volumes were measured 3 times a week in 2 dimensions using a caliper and the volume expressed in mm3 using the formula V=0.5 a×b2 where a and b are the long and short diameters of the tumor, respectively. Dosing was continued for 28 days, but any mouse in poor condition or with a tumor exceeding 3000 mm3 was terminated. For comparison between two groups an independent sample t-test was used; for comparison among three or more groups a one-way ANOVA was performed followed by multiple comparison procedures. A p-value <0.05 was considered to be statistically significant. The effect of CORT125134 in combination with paclitaxel in a triple negative breast cancer (TNBC) mouse xenograft model is shown in FIG. 2. Data represent mean+SEM. The administration of paclitaxel at a dose of 5 mg/kg was ineffective in this model, p=not significant compared with vehicle treated mice. The combination of paclitaxel and CORT125134 achieved a significant inhibition of tumor growth compared to vehicle treated mice (p<0.05) or compared to the use of paclitaxel alone (p<0.05).

Figure 3:
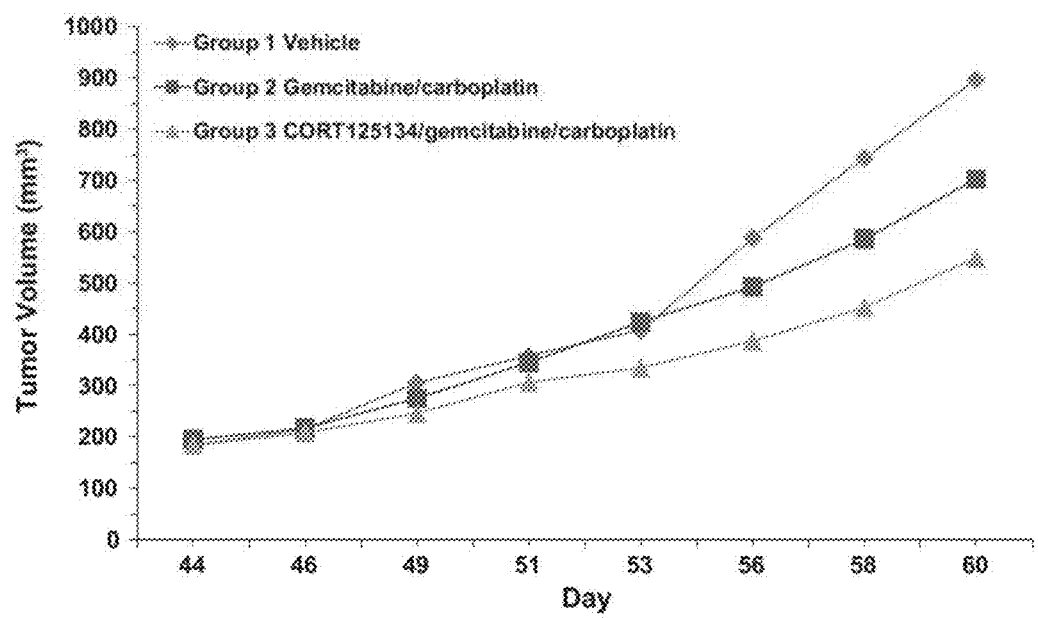
FIG. 3 shows the effect of CORT125134 in combination with gemcitabine/carboplatin in an ovarian cancer mouse xenograft model. 10 mice per group, CORT125134 was administered intraperitoneally (i.p.) on days 43, 44, 50 and 51, and gemcitabine/carboplatin was administered i.p. on days 44 and 51. Data represent mean values.

Example 3. Treating Ovarian Cancer Explants with CORT125134 in Combination with Gemcitabine/Carboplatin The effect of CORT125134 in combination with gemcitabine/carboplatin in an ovarian cancer mouse xenograft model is shown in FIG. 3 presenting results from groups of 10 mice per group. CORT125134 was administered intraperitoneally (i.p.) on days 43, 44, 50 and 51, and gemcitabine/carboplatin was administered i.p. on days 44 and 51. Data represent mean values. SK-OV-3 cells (5 million cells per mouse) were injected in the right flank of female Balb/c nude mice. When tumors reached a volume of 200 mm$^3$ the mice were randomized into groups of 10 and treatment was initiated. Mice were treated as follows: group 1 received vehicle on dosing days 1, 2, 8 and 9, group 2 received gemcitabine (80 mg/kg i.p.) and carboplatin (15 mg/kg i.p.) on dosing days 2 and 9 and group 3 received gemcitabine/carboplatin in the same regimen as group 2, +CORT125134 (20 mg/kg i.p.) on dosing days 1, 2, 8 and 9. Tumor volumes were measured 3 times a week and tumor volumes were calculated as detailed above. Any mouse in poor condition or with a tumor exceeding 2000 mm³ was terminated. The results were analyzed as indicated in Example 2 above. The administration of gemcitabine/carboplatin at these doses was ineffective in the SK-OV-3 model (p=NS vs vehicle-treated mice). The combination of gemcitabine/carboplatin with CORT125134 achieved a significant inhibition of tumor growth compared to vehicle (p<0.001), and compared with carboplatin/gemcitabine (p<0.01).

Example 4. Treating Prostate Cancer Explants with CORT125134 in Castrated Mice

Figure 4:
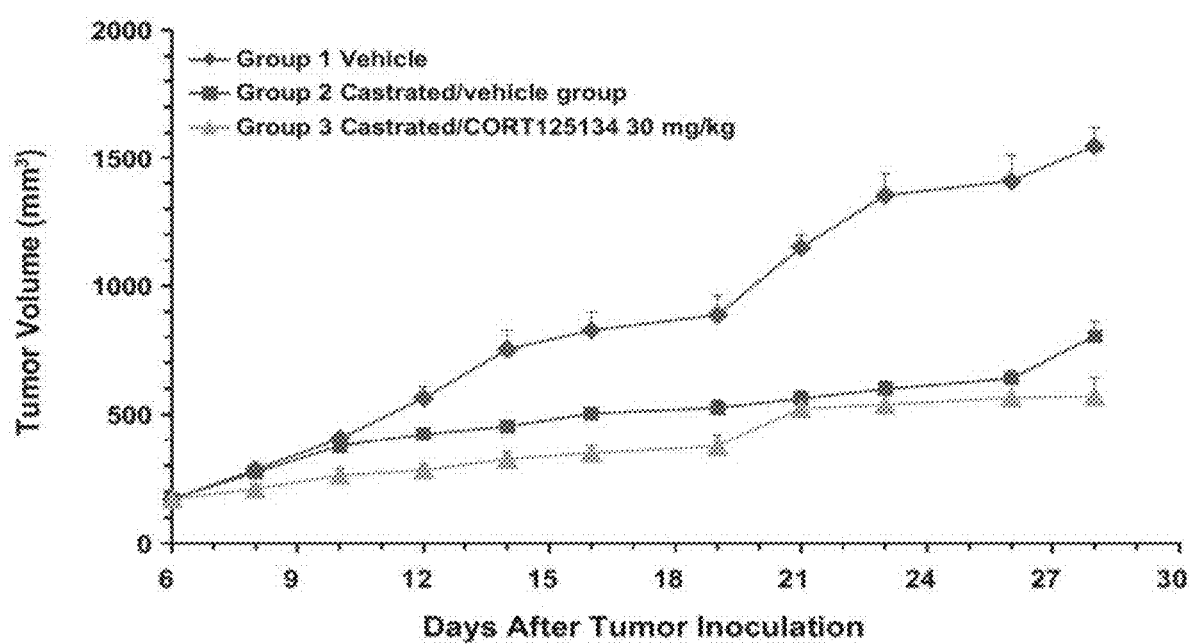
FIG. 4 shows the effect of CORT125134 in combination with castration in a prostate cancer (CRPC) mouse xenograft model. 10 mice per group, CORT125134 was administered orally daily for 21 days. Data represent mean+SEM.

The effect of CORT125134 in combination with castration in a prostate cancer (CRPC) mouse xenograft model is presented in FIG. 4. 22Rv1 cells (10 million cells per mouse) were injected in the right flank of male Balb/c nude mice. When the tumors reached a volume of 100-200 mm³ the mice were randomized into groups of 10 and then 2 of the 3 groups were castrated. Treatment was initiated the day after castration as follows: group 1 (not castrated) received vehicle, group 2 (castrated) received vehicle, and group 3 (castrated) received CORT125134 30 mg/kg orally (p.o.) daily for 21 days. Tumor volumes were measured 3 times a week as described previously. Any mouse in poor condition or with a tumor exceeding 3000 mm³ was terminated. The results were analyzed as indicated in Example 2 above. Data represent mean+SEM. Mice that were castrated exhibited reduced tumor growth compared with mice that were not castrated (p<0.0001). The administration of CORT125134 to castrated mice also inhibited tumor growth compared to mice that were not castrated (p<0.0001). The combination of castration and CORT125134 was more effective than castration alone (p<0.05).

Example 5. Treating a Patient Having Cervical Cancer with SGRM and an Chemotherapeutic Agent A 68-year-old female patient complains of upper abdomen pain. She is experiencing loss of appetite, nausea and vomiting episodes, and significant weight loss. A CT scan shows what is suspected to be a tumor in the cervix. The suspected tumor is confirmed by histological analysis to be a cancerous tumor. The patient is treated with CORT125134 at a dose of 200 mg once a day for eight weeks in combination with an intravenous infusion of nab-paclitaxel at a dose of 80 mg per square meter of body-surface area as an intravenous infusion over 30 minutes on days 1, 8, and 15 of every 28-day cycle. Tumor load is monitored using enhanced MRI before, during and after the treatment. The imaging indicate that tumor size is decreasing, and the reduction is more than 50% at the end of the treatment period.

What is claimed is:

1. A method of treating a subject hosting a cervical cancer tumor, the method comprising administering to the subject an effective amount of a chemotherapeutic agent and administering an effective amount of between about 1 mg/kg/day to about 30 mg/kg/day of a non-steroidal selective glucocorticoid receptor modulator (SGRM) to reduce the tumor load of the cervical cancer tumor, wherein the SGRM is a fused azadecalin compound having the following formula:

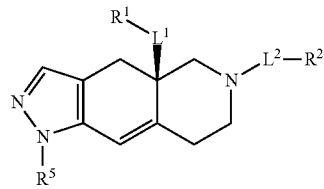

wherein
L¹ and L² are members independently selected from a bond and unsubstituted alkylene;
R¹ is a member selected from unsubstituted alkyl, unsubstituted heteroalkyl, unsubstituted heterocycloalkyl, —OR$^{1A}$, NR$^{1C}$R$^{1D}$, —C(O)NR$^{1C}$R$^{1D}$, and —C(O)OR$^{1A}$, wherein
R$^{1A}$ is a member selected from hydrogen, unsubstituted alkyl and unsubstituted heteroalkyl,
R$^{1C}$ and R$^{1D}$ are members independently selected from unsubstituted alkyl and unsubstituted heteroalkyl,
wherein R$^{1C}$ and R$^{1D}$ are optionally joined to form an unsubstituted ring with the nitrogen to which they are attached, wherein said ring optionally comprises an additional ring nitrogen;
R² has the formula:

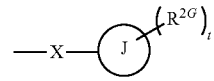

wherein
R$^{2G}$ is a member selected from hydrogen, halogen, unsubstituted alkyl, unsubstituted heteroalkyl, unsubstituted cycloalkyl, unsubstituted heterocycloalkyl, —CN, and —CF₃;
J is phenyl;
t is an integer from 0 to 5;
X is —S(O₂)—; and
R⁵ is phenyl optionally substituted with 1-5 R$^{5A}$ groups, wherein
R$^{5A}$ is a member selected from hydrogen, halogen, —OR$^{5A}$, S(O₂)NR$^{5A2}$R$^{5A3}$, —CN, and unsubstituted alkyl, wherein
R$^{5A1}$ is a member selected from hydrogen and unsubstituted alkyl, and
R$^{5A2}$ and R$^{5A3}$ are members independently selected from hydrogen and unsubstituted alkyl,
or salts and isomers thereof.

2. The method of claim 1, wherein the chemotherapeutic agent is selected from the group consisting of taxanes, alkylating agents, topoisomerase inhibitors, endoplasmic reticulum stress inducing agents, antimetabolites, mitotic inhibitors and combinations thereof.

3. The method of claim 2, wherein the chemotherapeutic agent is a taxane.

4. The method of claim 2, wherein the chemotherapeutic agent is selected from the group consisting of nab-paclitaxel, 5-fluorouracil (5-FU), gemcitabine, cisplatin and capecitabine.

5. The method of claim 1, wherein the fused azadecalin compound is (R)-(4a-ethoxymethyl-1-(4-fluorophenyl)-6-(4-trifluoromethyl-benzenesulfonyl)-4,4a,5,6,7,8-hexa-hydro-1H,1,2,6-triaza-cyclopenta[b]naphthalene, which has the formula:

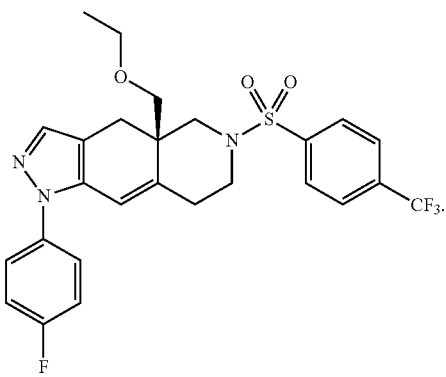 [SMILES: CCOC[C@]12Cc3cnn(-c4ccc(F)cc4)c3C=C1CCN(S(=O)(=O)c1ccc(C(F)(F)F)cc1)C2]

6. The method of claim 1, wherein said administration of said SGRM comprises oral administration of said SGRM.

7. The method of claim 6, wherein said oral administration of said SGRM comprises daily oral administration of said SGRM.

8. The method of claim 6, wherein said oral administration of said SGRM comprises oral administration of said SGRM on one or more days selected from the group consisting of a day before administration of said chemotherapeutic agent, the day of administration of said chemotherapeutic agent, and a day after administration of said chemotherapeutic agent.

9. The method of claim 6, wherein said oral administration of said SGRM comprises oral administration of said SGRM on the day of administration of said chemotherapeutic agent and also on one or both of a day before and a day after administration of said chemotherapeutic agent.

10. The method of claim 1, wherein said chemotherapeutic agent is selected from the group consisting of albumin-bound paclitaxel, chlorambucil, cyclophosphamide, ifosfamide, melphalan, streptozocin, carmustine, lomustine, bendamustine, uramustine, estramustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, campothecin, topotecan, 9-nitrocamptothecin, 9-aminocamptothecin, rubifen, gimatecan, diflomotecan, BN80927, DX-895 If, MAG-CPT, amsacrine, etoposide, etoposide phosphate, teniposide, paclitaxel, docetaxel, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, Irinotecan, Oxaliplatin, Cisplatin, irinotecan liposome, and combinations thereof.

11. A method of treating a subject hosting a cervical cancer tumor, the method comprising administering to the subject an effective amount of a chemotherapeutic agent and administering an effective amount of between about 1 mg/kg/day to about 30 mg/kg/day of a non-steroidal selective glucocorticoid receptor modulator (SGRM) to reduce the tumor load of the cervical cancer tumor, wherein the SGRM is an octahydro fused azadecalin compound having the following formula:

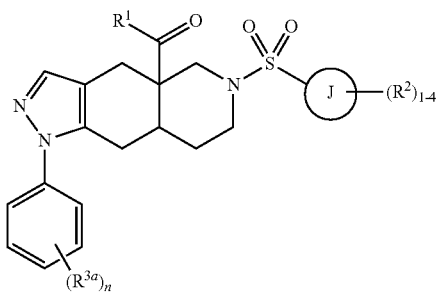

wherein
$R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S;

alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2e}$ groups;

$R^{2a}$, $R^{2b}$ and $R^{2c}$ are each independently selected from the group consisting of hydrogen and $C_{1-6}$ alkyl;

each $R^{3a}$ is independently halogen; and subscript n is an integer from 0 to 3, or salts and isomers thereof.

12. The method of claim 11, wherein the octahydro fused azadecalin compound is ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, which has the formula:

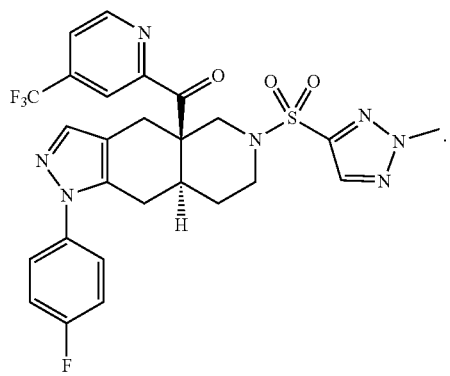 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

13. The method of claim 11, wherein said administration of said SGRM comprises oral administration of said SGRM.

14. The method of claim 13, wherein said oral administration of said SGRM comprises daily oral administration of said SGRM.

15. The method of claim 13, wherein said oral administration of said SGRM comprises oral administration of said SGRM on one or more days selected from the group consisting of a day before administration of said chemotherapeutic agent, the day of administration of said chemotherapeutic agent, and a day after administration of said chemotherapeutic agent.

16. The method of claim 13, wherein said oral administration of said SGRM comprises oral administration of said SGRM on the day of administration of said chemotherapeutic agent and also on one or both of a day before and a day after administration of said chemotherapeutic agent.

17. The method of claim 11, wherein the chemotherapeutic agent is selected from the group consisting of taxanes, alkylating agents, topoisomerase inhibitors, endoplasmic reticulum stress inducing agents, antimetabolites, mitotic inhibitors and combinations thereof.

18. The method of claim 11, wherein the chemotherapeutic agent is selected from the group consisting of nab-paclitaxel, 5-fluorouracil (5-FU), gemcitabine, cisplatin and capecitabine.

19. The method of claim 11, wherein the chemotherapeutic agent is a taxane.

20. The method of claim 11, wherein said chemotherapeutic agent is selected from the group consisting of albumin-bound paclitaxel, chlorambucil, cyclophosphamide, ifosfamide, melphalan, streptozocin, carmustine, lomustine, bendamustine, uramustine, estramustine, nimustine, ranimustine, mannosulfan busulfan, dacarbazine, temozolomide, thiotepa, altretamine, 5-fluorouracil (5-FU), 6-mercaptopurine (6-MP), capecitabine, cytarabine, floxuridine, fludarabine, gemcitabine, hydroxyurea, methotrexate, pemetrexed, daunorubicin, doxorubicin, epirubicin, idarubicin, SN-38, ARC, NPC, campothecin, topotecan, 9-nitrocamptothecin, 9-aminocamptothecin, rubifen, gimatecan, diflomotecan, BN80927, DX-895 If, MAG-CPT, amsacrine, etoposide, etoposide phosphate, teniposide, paclitaxel, docetaxel, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, Irinotecan, Oxaliplatin, Cisplatin, irinotecan liposome, and combinations thereof.

\* \* \* \* \*

UNITED STATES PATENT AND TRADEMARK OFFICE
CERTIFICATE OF CORRECTION

PATENT NO. : 10,898,478 B2
APPLICATION NO. : 16/742198
DATED : January 26, 2021
INVENTOR(S) : Hazel Hunt It is certified that error appears in the above-identified patent and that said Letters Patent is hereby corrected as shown below:

In the Claims

In Column 36, Lines 16 and 17, Claim 1, delete "—$OR^{1A}$, $NR^{1C}R^{1D}$, —$C(O)NR^{1C}R^{1D}$, and —$C(O)OR^{1A}$, wherein" and replace with
-- –$OR^{1A}$, $NR^{1C}R^{1D}$, –$C(O)NR^{1C}R^{1D}$, and –$C(O)OR^{1A}$, wherein --

In Column 36, Lines 37-38, Claim 1, delete "—CN, and —$CF_3$;" and replace with
-- –CN, and –$CF_3$; --

In Column 36, Line 41, Claim 1, delete "—$S(O_2)$—;" and replace with -- –$S(O_2)$–; --

In Column 36, Line 45, Claim 1, delete "—$OR^{5A}$, $S(O_2)NR^{5A2}R^{5A3}$, —CN," and replace with
-- –$OR^{5A1}$, $S(O_2)NR^{5A2}R^{5A3}$, –CN, --

In Column 38, Line 40, Claim 11, delete "$R^{2e}$" and replace with -- $R^{2c}$ --

Signed and Sealed this
Fifth Day of October, 2021

Drew Hirshfeld
*Performing the Functions and Duties of the
Under Secretary of Commerce for Intellectual Property and
Director of the United States Patent and Trademark Office*